US011457901B2

(12) United States Patent
Toft et al.

(10) Patent No.: US 11,457,901 B2
(45) Date of Patent: Oct. 4, 2022

(54) TISSUE COLLECTION DEVICE FOR COLLECTION OF ONE OR MORE TISSUE SAMPLES FROM A BIOPSY NEEDLE OR BIOPSY DEVICE AND BIOPSY DEVICE COMPRISING SUCH A TISSUE COLLECTION DEVICE

(71) Applicant: TeesuVac ApS, Hørsholm (DK)

(72) Inventors: Tue Kjaergaard Toft, Copenhagen N (DK); Lars Ulrik Nielsen, Virum (DK); Keld Sloth Christensen, Hjerm (DK); Søren Kjeld Kjellerup Hansen, Fjenneslev (DK); Tomas Gundberg, Viby Sjælland (DK); Henrik Harboe, Copenhagen K (DK); Ole Kjeldsen, Struer (DK)

(73) Assignee: TeesuVac ApS, Hørsholm (DK)

(*) Notice: Subject to any disclaimer, the term of this patent is extended or adjusted under 35 U.S.C. 154(b) by 416 days.

(21) Appl. No.: 16/349,477

(22) PCT Filed: Nov. 13, 2017

(86) PCT No.: PCT/EP2017/079065
§ 371 (c)(1),
(2) Date: May 13, 2019

(87) PCT Pub. No.: WO2018/087367
PCT Pub. Date: May 17, 2018

(65) Prior Publication Data
US 2020/0187922 A1 Jun. 18, 2020

(30) Foreign Application Priority Data

Nov. 12, 2016 (DK) .............................. PA201670902

(51) Int. Cl.
*A61B 10/02* (2006.01)
*A61B 10/00* (2006.01)
(52) U.S. Cl.
CPC ...... *A61B 10/0275* (2013.01); *A61B 10/0096* (2013.01); *A61B 2010/0225* (2013.01)
(58) Field of Classification Search
CPC . A61B 10/0096; A61B 10/0275; A61B 10/02; A61B 2010/0225
See application file for complete search history.

(56) References Cited

U.S. PATENT DOCUMENTS 9,345,457 B2      5/2016  Speeg et al.
2003/0198574 A1  10/2003  Studer
(Continued)

FOREIGN PATENT DOCUMENTS

CA     2647748 A1    10/2007
JP     2008-128749 A  6/2008
(Continued)

OTHER PUBLICATIONS

International Search Report and Written Opinion of International Searching Authority for Application No. PCT/EP2017/079065, dated May 11, 2018 (19 pages).

*Primary Examiner* — Alex M Valvis
*Assistant Examiner* — Anna Roberts
(74) *Attorney, Agent, or Firm* — Nixon Peabody LLP

(57) ABSTRACT

A tissue collection device (1) for collection of one or more exposed tissue samples (2) from a biopsy needle or biopsy device, which tissue collection device comprises one or more pieces of a carrier medium (6) and is arranged to temporarily bring a piece of carrier medium into physical contact with the tissue sample, while the tissue sample is still positioned in the biopsy needle or biopsy device, so that the tissue sample (2) adheres to the carrier medium (6) and is (Continued)

Figure 1C:
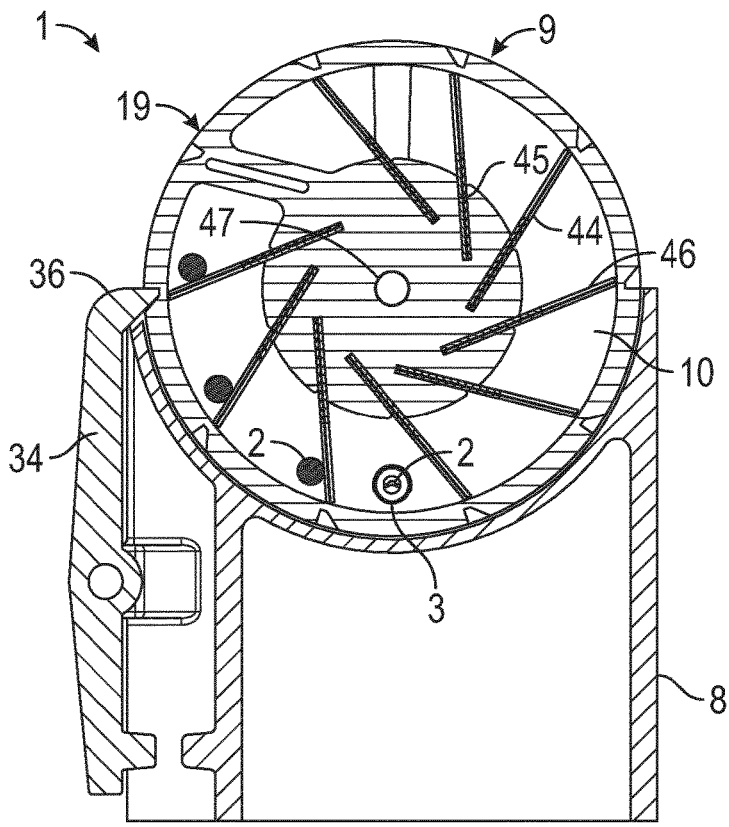

removed from the biopsy needle (3) or biopsy device (4) with the carrier medium (6), when the carrier medium (6) is removed from the biopsy needle or biopsy device again. Furthermore, a biopsy device comprising such a tissue collection device is disclosed.

18 Claims, 22 Drawing Sheets

(56) References Cited

U.S. PATENT DOCUMENTS

| | | |
|---|---|---|
| 2008/0214955 A1 | 9/2008 | Speeg |
| 2009/0050516 A1 | 2/2009 | Hardin |
| 2010/0160816 A1 | 6/2010 | Parihar |
| 2011/0054350 A1 | 3/2011 | Videbaek |
| 2013/0267870 A1 | 10/2013 | Lonky |
| 2015/0305722 A1 | 10/2015 | Nevo |
| 2016/0081883 A1* | 3/2016 | Saltsov ................. A61J 7/0084 221/2 |
| 2016/0242748 A1* | 8/2016 | Pasternak ................. B01L 9/52 |

FOREIGN PATENT DOCUMENTS

| | | | |
|---|---|---|---|
| WO | WO 2007/112751 A2 | 10/2007 | |
| WO | WO-2007112751 A2 * | 10/2007 | ............. A61B 90/30 |
| WO | WO-2011158782 A1 * | 12/2011 | ............... C21D 9/30 |

\* cited by examiner

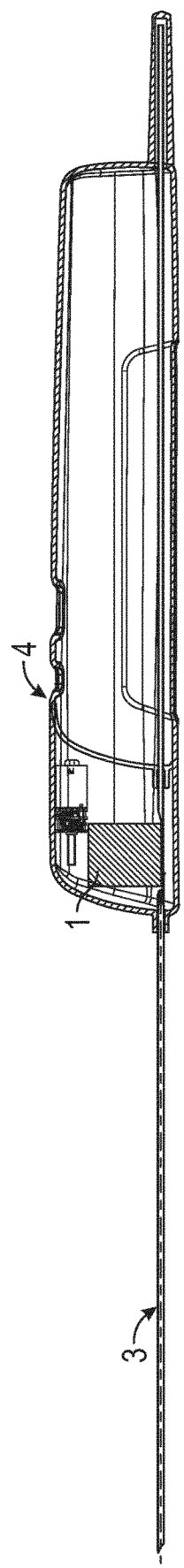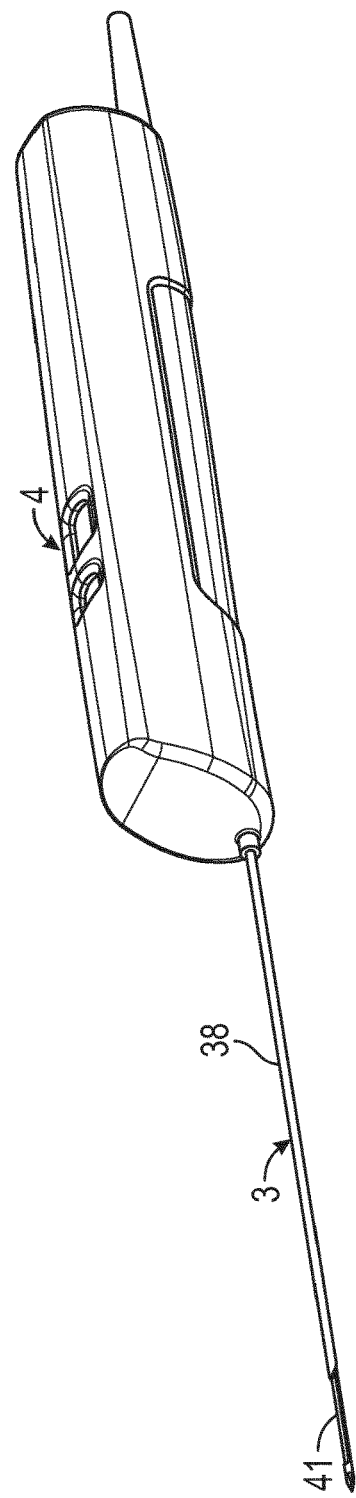

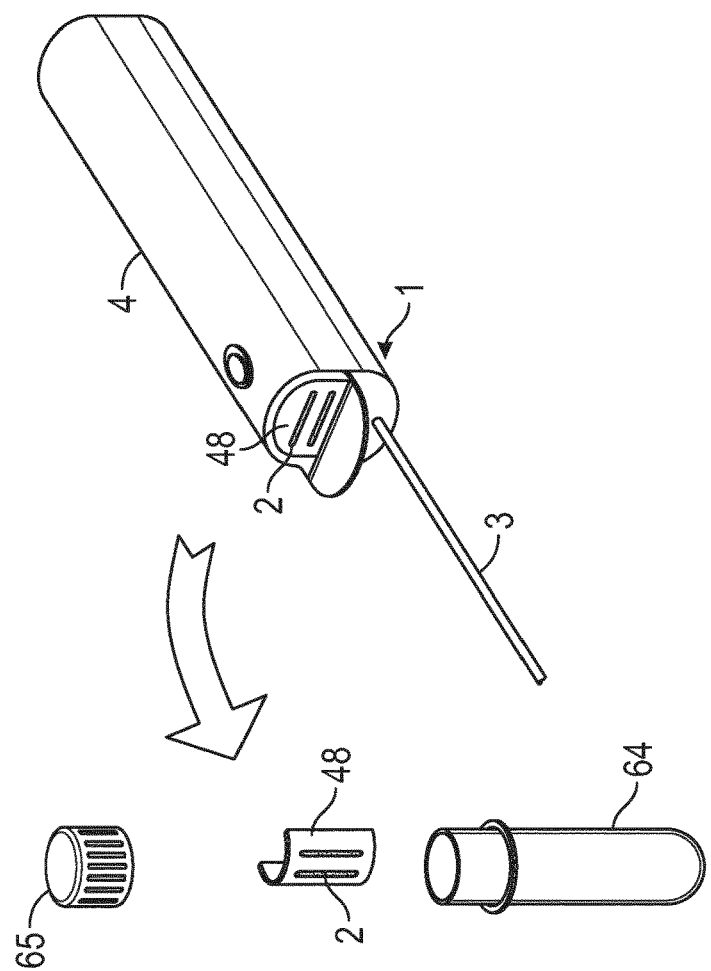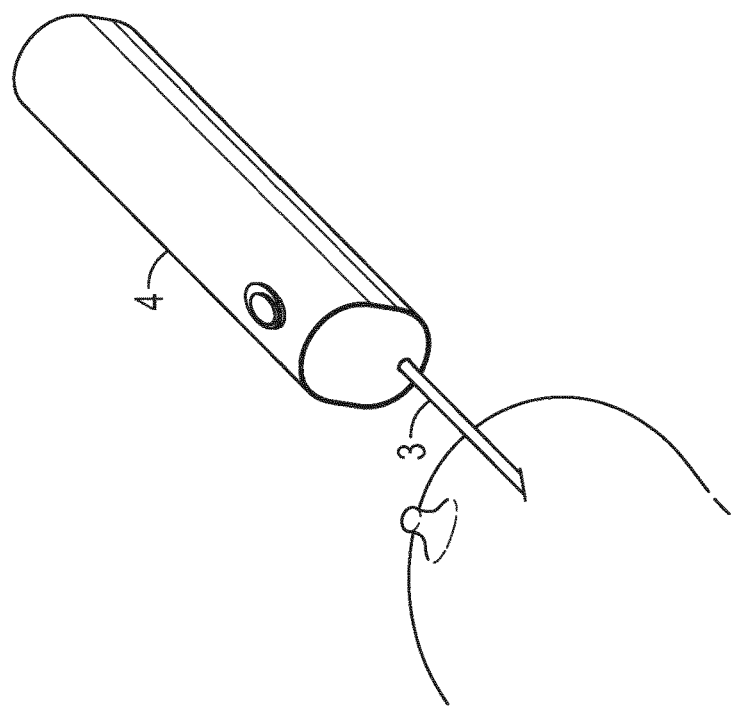
FIG. 7

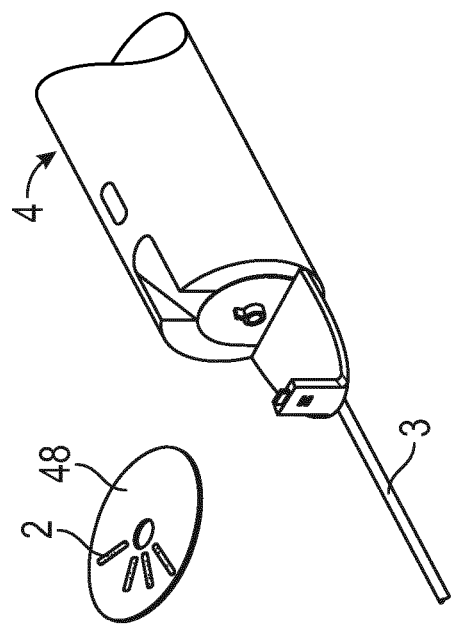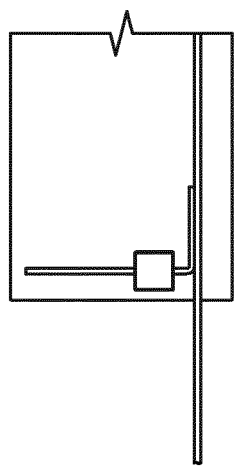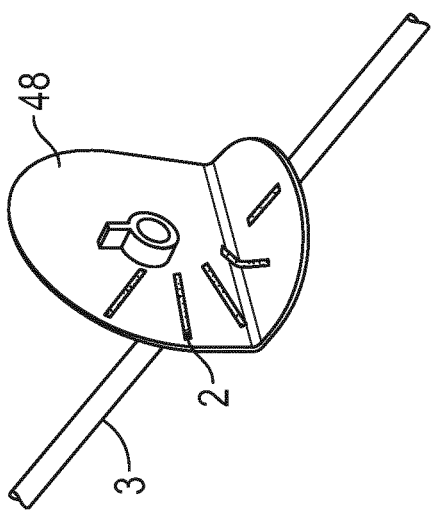
FIG. 10

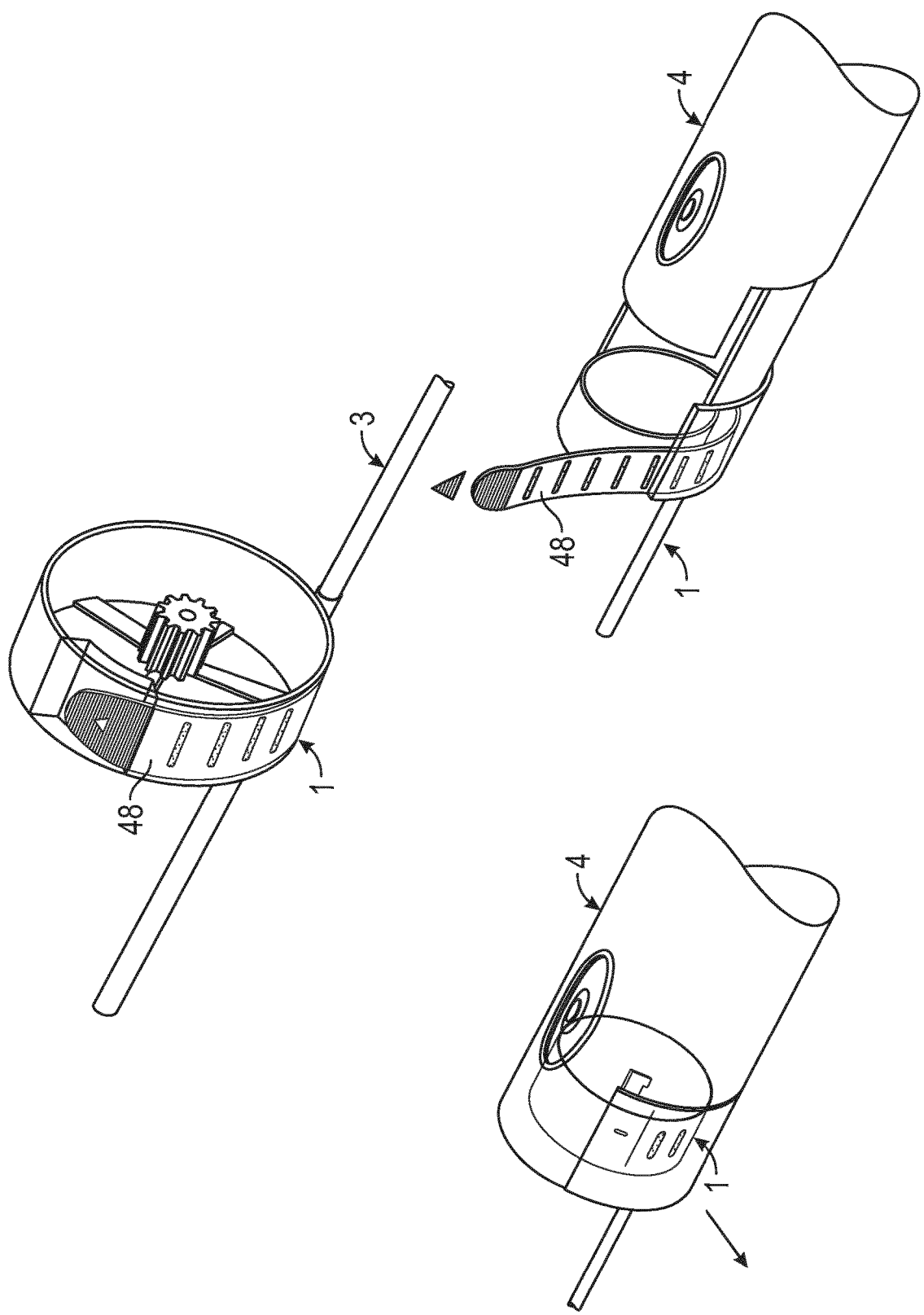

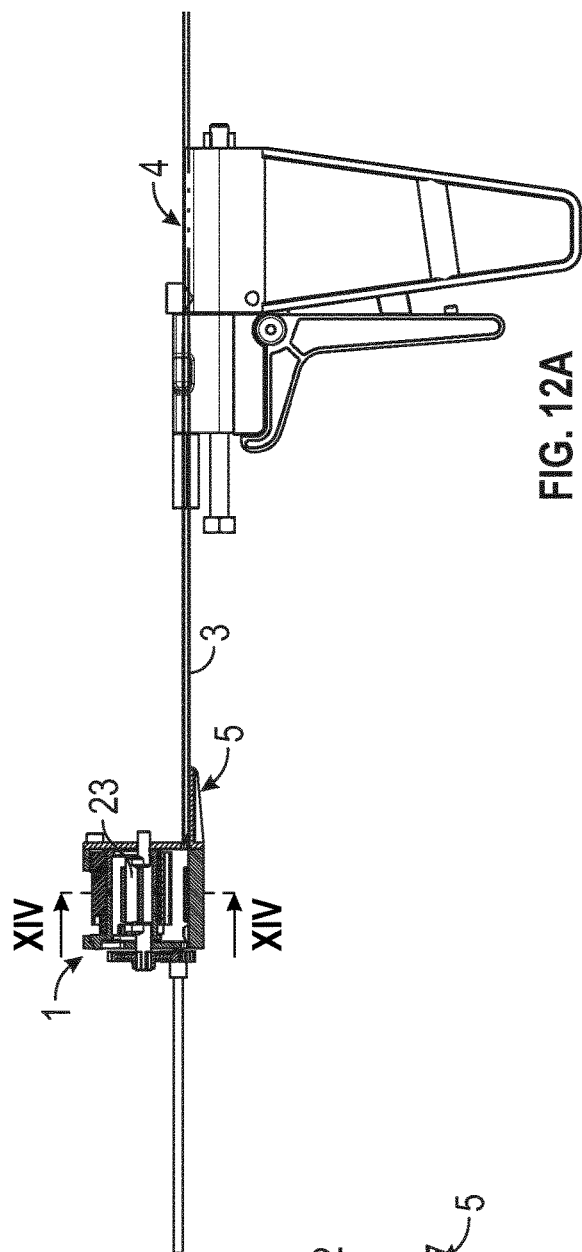
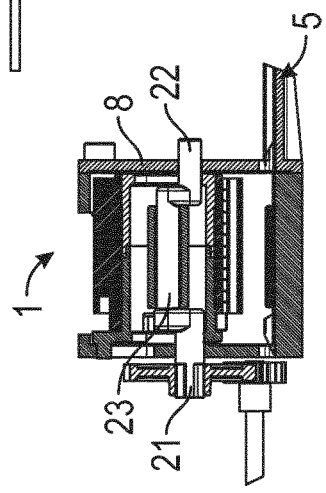
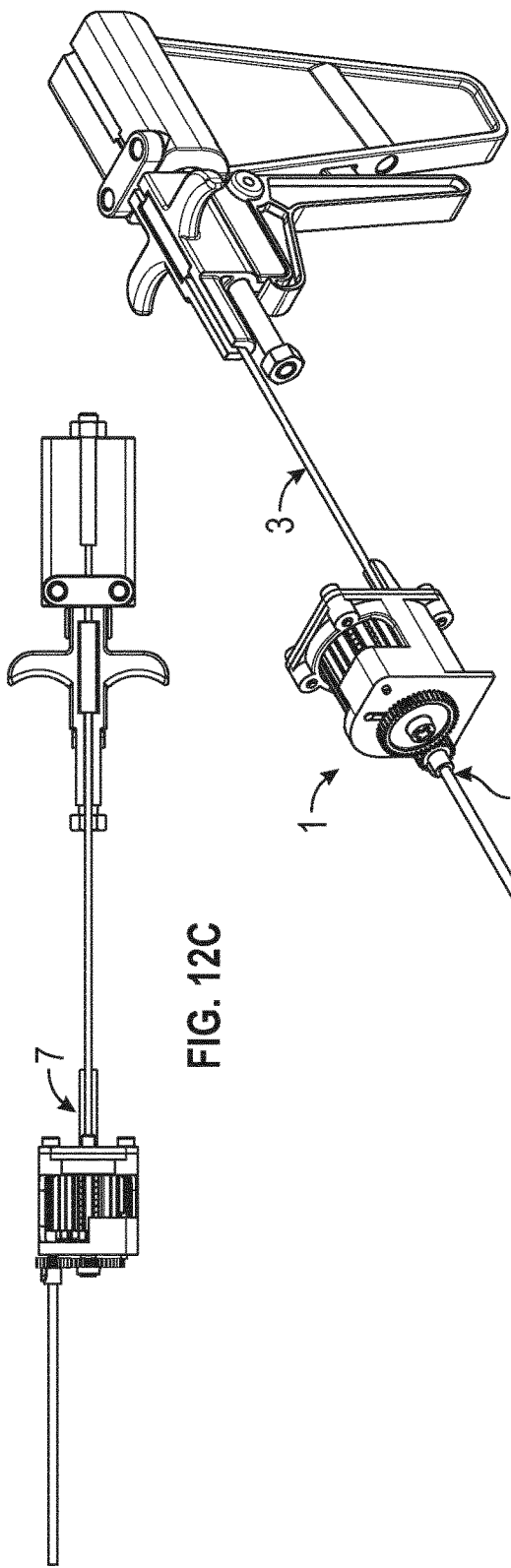
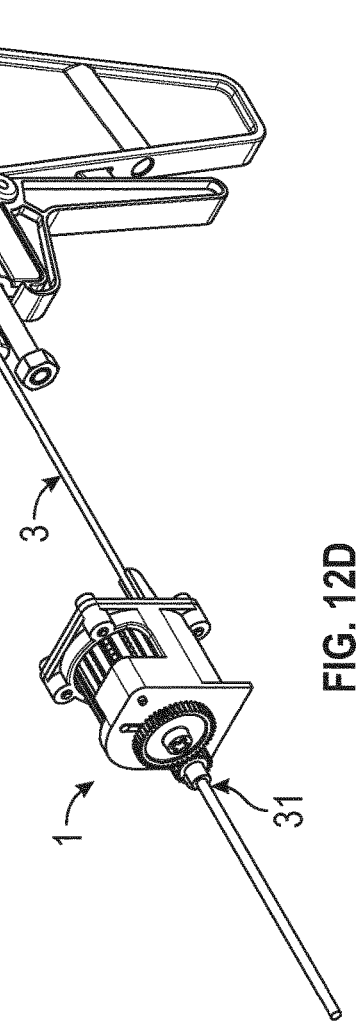
FIG. 12A
FIG. 12B
FIG. 12C
FIG. 12D

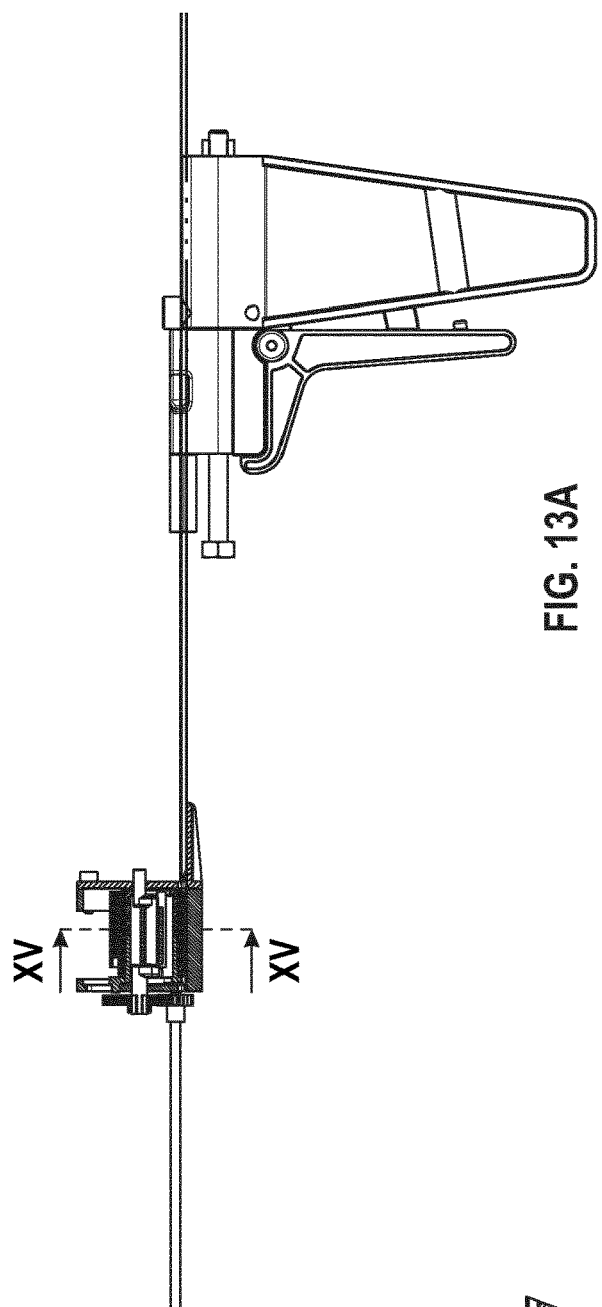
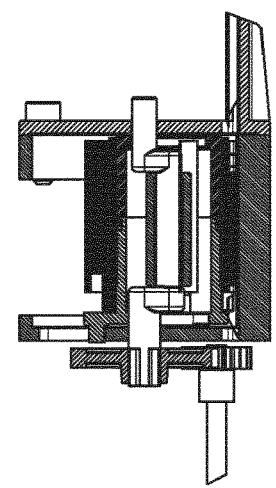
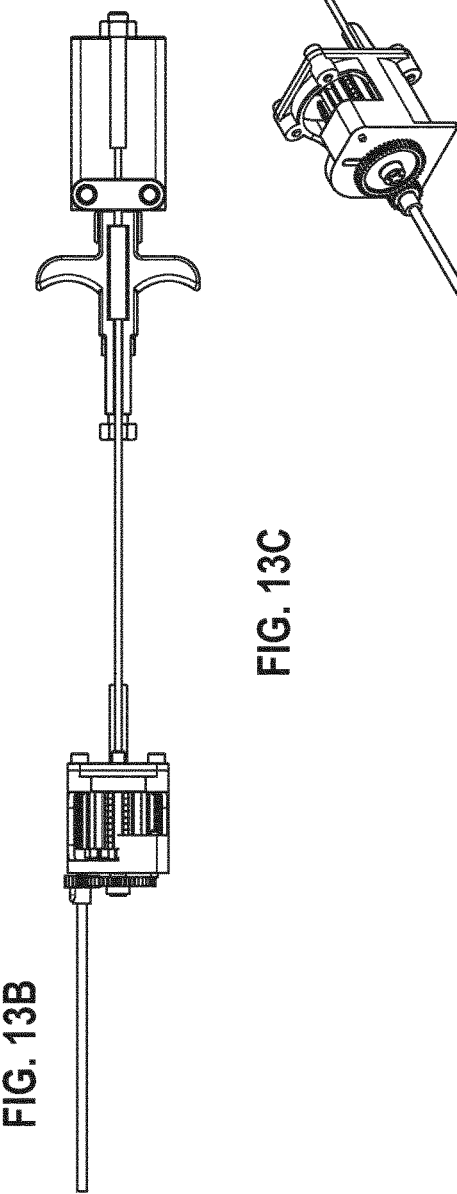
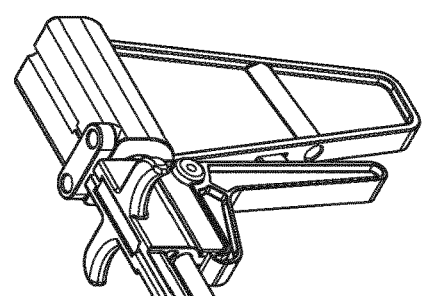
FIG. 13A
FIG. 13B
FIG. 13C
FIG. 13D

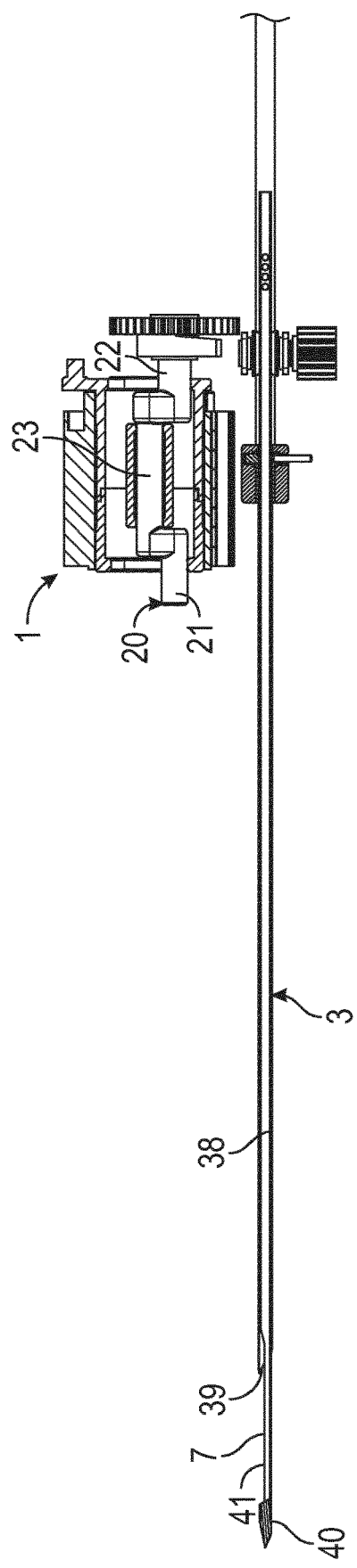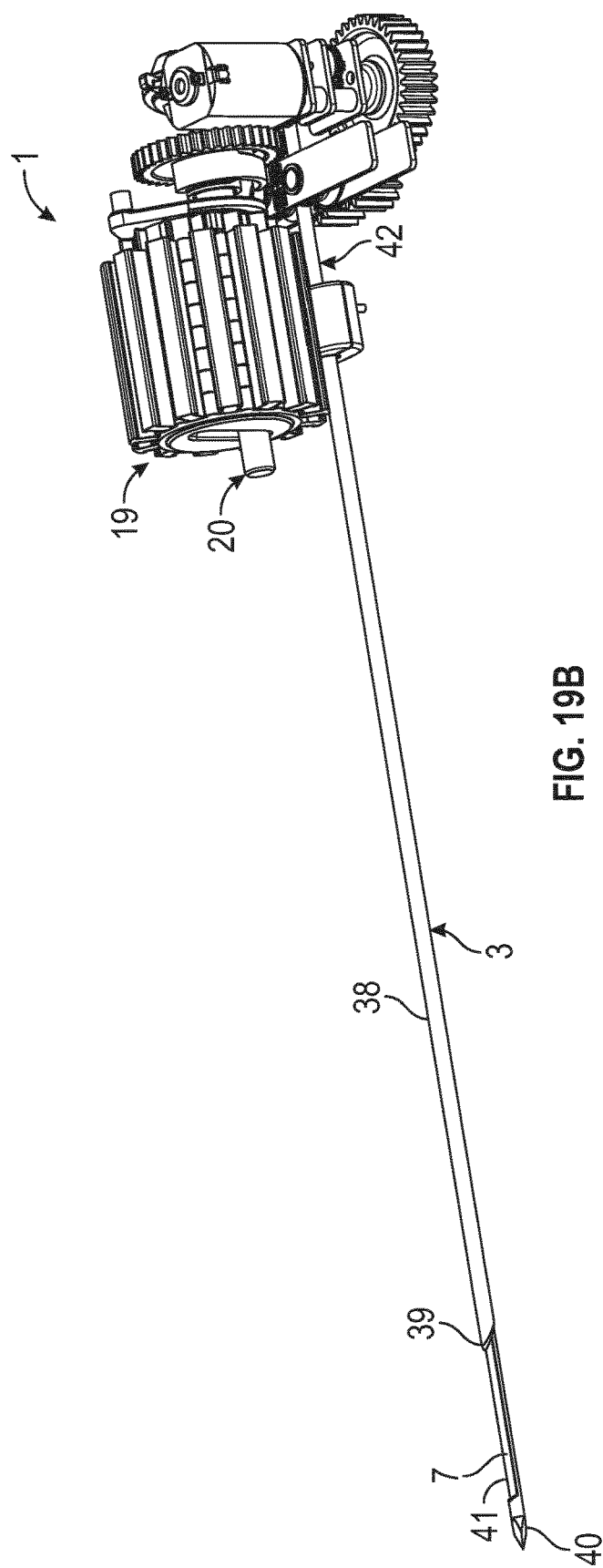
FIG. 19A
FIG. 19B

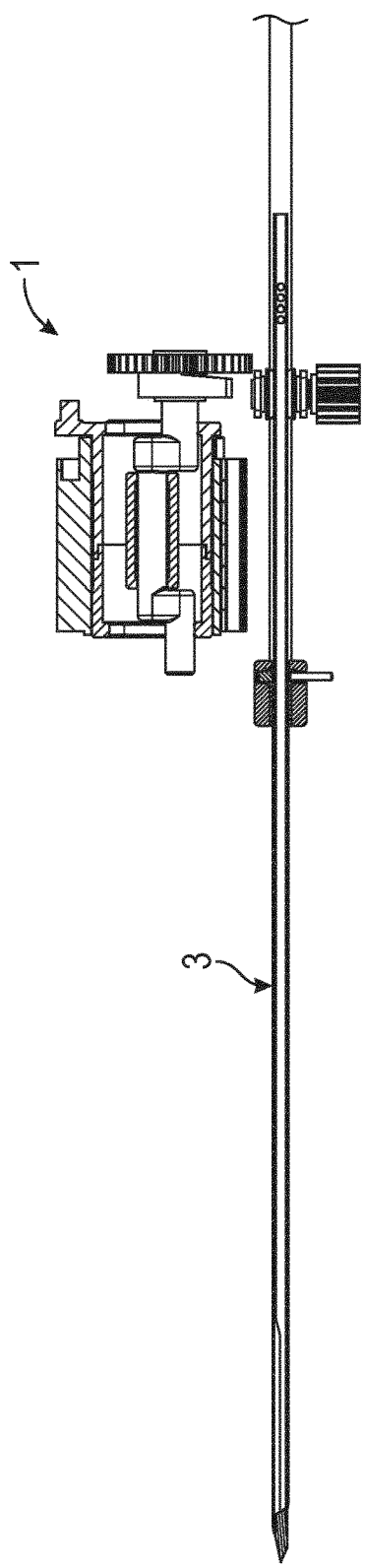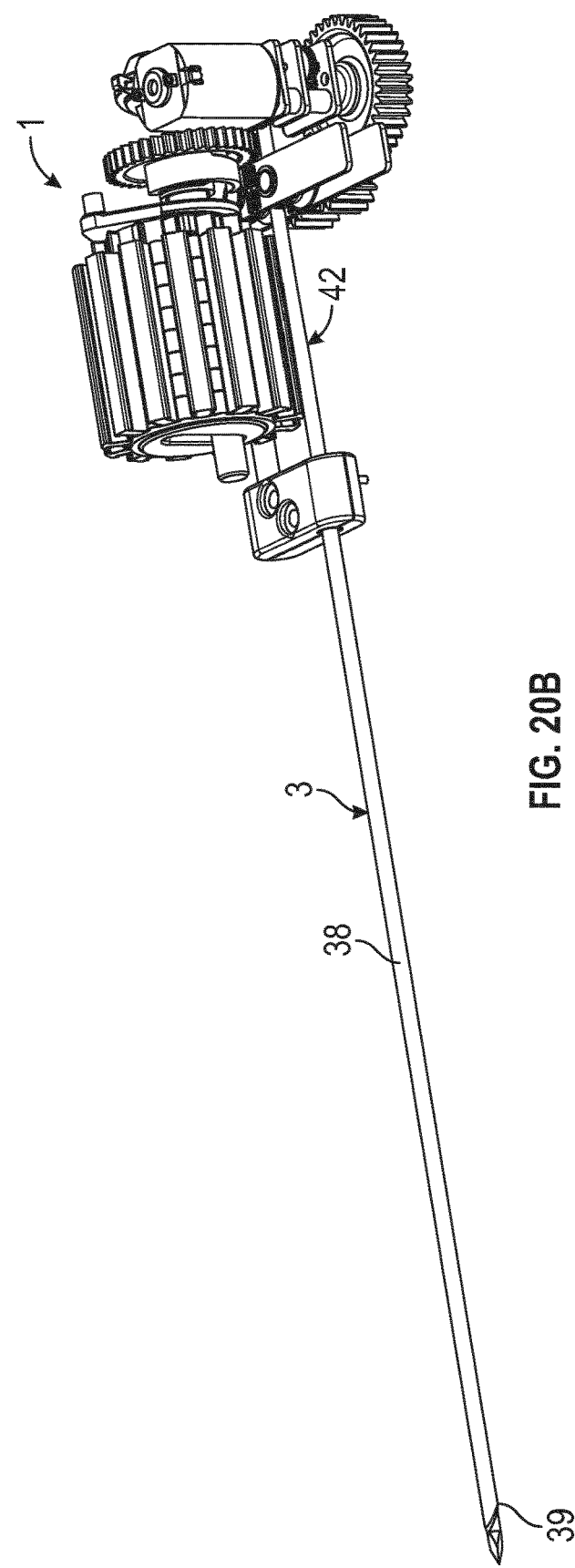
FIG. 20A
FIG. 20B

TISSUE COLLECTION DEVICE FOR COLLECTION OF ONE OR MORE TISSUE SAMPLES FROM A BIOPSY NEEDLE OR BIOPSY DEVICE AND BIOPSY DEVICE COMPRISING SUCH A TISSUE COLLECTION DEVICE

CROSS-REFERENCE TO RELATED APPLICATIONS

This application is U.S. National Stage of International Application No. PCT/EP2017/079065, filed Nov. 13, 2017, which claims the benefit of and priority to Denmark Patent Application No. PA 2016 70902, filed Nov. 12, 2016, all of which are incorporated herein by reference in their entireties.

The present invention relates to a tissue collection device for collection of one or more tissue samples from a biopsy needle or biopsy device, in particular the type of biopsy needle or biopsy device comprising an outer cutting needle and an inner needle with a tissue compartment for the tissue sample, and to a biopsy device comprising such a tissue collection device.

BACKGROUND OF THE INVENTION

In a well-known type of biopsy devices, a tissue sample is severed by an outer cutting needle surrounding and sliding along an inner needle, in which there is a tissue compartment in the form of an indentation or a side-opening shaped as a form of tray or, in some cases, in the form of a canoe. Typically, when the biopsy needle is inserted into the target tissue, a tissue part is squeezed into this tissue compartment by the surrounding tissue or it can be sucked into the tissue compartment by means of vacuum before the cutting needle is activated, whereby the severed tissue sample is deposited in the tissue compartment of the inner needle.

In order to collect the sample and prepare the biopsy device for obtaining the next tissue sample, the biopsy device is withdrawn from the patient and the part of the inner needle comprising the tissue compartment is exposed, either via a side opening in the outer cutting needle or by sliding the tissue compartment out of one of the ends of the outer cutting needle, in order to create access to the tissue sample deposited in the tissue compartment therein.

The tissue sample, which is normally but not always in the shape of a cylinder (depending of the in the structure and solidity of the sample), is then manually removed from the tissue compartment of the inner needle. This is typically done by rotating the biopsy needle or biopsy device while pressing the exposed tissue sample therein against a small piece of biopsy paper arranged on a tabletop or the like. When the desired number of tissue samples have been collected, the small pieces of biopsy paper each holding a tissue sample are then prepared appropriately and sent to a laboratory for examination.

Apart from the obvious challenges related to keeping track of and distinguishing between a sometimes relatively large number of such small paper pieces each with one or more tissue sample, it requires a certain amount of skills and experience to successfully remove tissue samples from biopsy needles this way. One specific challenge is to keep the small piece of paper in place while "rolling" the tissue sample from the inner needle onto the paper. Another is to avoid destroying the physical structure of the tissue sample and, thereby, losing valuable information about tissue morphology, which could otherwise be obtained therefrom, when performing the actual combination of rotation of the needle and pressure against the biopsy paper. Experience shows that far from all staff working with biopsy devices possess these intricate skills.

US 2008/0214955 A1 discloses a biopsy device including a cutter defining a cutter lumen and a tissue sample holder for collecting tissue samples. In one example, the tissue sample holder includes a rotatable manifold, and has a plurality of chambers that are each configured to separately hold tissue samples. A tissue sample holder rotation mechanism is operable to rotate the manifold to successively align each of the chambers with the cutter lumen. A severed tissue sample may travel proximally through the cutter lumen to the tissue sample holder by application of vacuum.

US 2013/0267870 A1 discloses a frictional tissue sampling device with an expandable balloon and associated abrasive material that can be used to obtain tissue biopsy samples. A frictional tissue sampling device with expandable abrasive material can be used to obtain an epithelial tissue biopsy sample from lesions. The device can be otherwise used to sample specific locations. In various embodiments, the head of the device can be passes through a catheter into a body canal to sample epithelial tissue.

BRIEF DESCRIPTION OF THE INVENTION

It is an object of the present invention to provide a tissue collection device, which safely and gently performs the removal of one or more tissue samples from a biopsy needle or biopsy device and preferably overcomes the above-mentioned disadvantage of the solutions and methods known in the art.

The present invention relates to a tissue collection device for collection of one or more exposed tissue samples from a biopsy needle or biopsy device which tissue collection device comprises one or more pieces of a carrier medium and is arranged to temporarily bring a piece of carrier medium into physical contact with the tissue sample, while the tissue sample is still positioned in the biopsy needle or biopsy device, so that the tissue sample adheres to the carrier medium and is removed from the biopsy needle or biopsy device with the carrier medium, when the carrier medium is removed from the biopsy needle or biopsy device again.

By bringing the carrier medium into physical contact with the tissue sample so that the tissue sample adheres to the carrier medium and subsequently removing the carrier medium with the tissue sample from the biopsy needle or biopsy device, the tissue sample may be removed and collected from the biopsy needle or biopsy device in a gentle and controlled manner.

In an embodiment of the invention, access to a tissue sample inside a biopsy needle is made available through exposing a tissue compartment therein.

In an embodiment of the invention, the tissue collection device is configured to automatically collect the tissue sample from the biopsy needle or biopsy device when the exposed tissue sample therein is placed at a predefined position relative to the tissue collection device. Thereby, the operation of the device by the user may be facilitated.

In an embodiment of the invention, the pieces of carrier mediums consist of pieces of a paper material, such as for instance biopsy paper.

In an embodiment of the invention, the carrier medium includes a liquid absorbing material. Thereby, because a tissue sample typically has a high content of fluid, it may be ensured that the tissue sample may adhere to the carrier medium.

In an embodiment of the invention, the carrier medium has a porous sample contacting surface. Thereby, because a tissue sample typically has a high content of fluid, it may be ensured that the tissue sample may adhere to the carrier medium.

Other carrier mediums, which are capable of making tissue samples adhere to them, may also be used, such as sponges, cloth, felt leather, metal, glass, plastic materials or combinations thereof.

In an embodiment of the invention, the tissue collection device further comprises a sample storage with a plurality of sample compartments, each arranged to hold a tissue sample collected from a biopsy needle or biopsy device, in such a way that the collected samples are indexed and kept separately in substantially the same shape as they had in the biopsy needle or biopsy device. Thereby, it may be ensured that the tissue samples are stored in a controlled way without risk of mixing up the samples. Furthermore, it may be advantageous that the tissue samples are maintained in substantially the same shape as they had in the biopsy needle or biopsy device, because any squeezing or deformation of tissue samples may reduce the structure and thereby the quality of the samples.

In an embodiment of the invention, the sample storage is configured as a wheel, in which the sample compartments are arranged along the periphery of the wheel.

In an embodiment of the invention, the sample compartments are separated by pieces of carrier medium, each of which is fastened in the side closest to the centre of the sample storage only and is optionally supported by a piece of a more rigid but still resilient supporting material, and the sample storage is arranged to be rotated in angular steps corresponding to the distance between two neighbouring sample compartments in such a way that, when the part of a biopsy needle or biopsy device holding a tissue sample is inserted in a direction parallel to the rotational axis of the sample storage into an empty sample compartment thereof and the sample storage is rotated one step, a piece of carrier medium separating the sample compartment in question and a neighbouring sample compartment will be drawn across the biopsy needle or biopsy device, the tissue sample in the biopsy needle or biopsy device adheres to the piece of carrier medium and follows it, as it passes the biopsy needle or biopsy device, leaving the biopsy needle or biopsy device empty in the neighbouring empty sample compartment.

In an embodiment of the invention, each of the sample compartments is open through the periphery of the sample storage and lined with a piece of carrier medium, and the sample storage is arranged to be rotated in angular steps corresponding to the distance between two neighbouring sample compartments and to be able to move forth and back in a given radial direction in such a way that, when the part of a biopsy needle or biopsy device holding a tissue sample is arranged adjacent an empty sample compartment of the sample storage in the radial direction in which the sample storage is able to move forth and back, the sample storage can move towards the biopsy needle or biopsy device so that the empty sample compartment surrounds the biopsy needle or biopsy device and the tissue sample therein, the tissue sample in the biopsy needle or biopsy device adheres to the piece of carrier medium and follows it, when the sample storage moves back and away from the biopsy needle or biopsy device again, before it rotates one step to place a new empty sample compartment in the position corresponding to the radial direction in which it can move forth and back.

In an embodiment of the invention, the tissue collection device is arranged to press temporarily a piece of carrier medium against a tissue sample within a biopsy needle or biopsy device, whereby the tissue sample adheres to the carrier medium and is lifted away from the biopsy needle or biopsy device by the carrier medium, when the pressure onto the carrier medium is released. By pressing the carrier medium against a tissue sample, the tissue sample may adhere even better to the carrier medium.

In an embodiment of the invention, a single piece of carrier medium is arranged to collect a plurality of tissue samples, for instance by being moved stepwise in a direction between successive collections of a tissue sample from the same or a different biopsy needle or biopsy device.

In an embodiment of the invention, the tissue collection device is arranged to press a piece of carrier medium into the biopsy needle or biopsy device after having removed the tissue sample therefrom for cleansing the biopsy needle or biopsy device by sucking up any remaining tissue therein.

In an embodiment, the carrier medium included by the tissue collection device is adapted to adhere to a tissue sample.

In an embodiment, the tissue collection device includes a tissue sample positioning arrangement adapted to receive and/or support a biopsy needle or biopsy device holding a tissue sample. Thereby, a controlled tissue collection operation may be achieved by ensuring correct positioning of the biopsy needle or biopsy device during the tissue collection operation whereby the tissue samples may be collected in a consistent way without risk of squeezing or deforming the tissue samples.

In an embodiment, the tissue collection device is adapted to perform a tissue collection operation by relative movement between the carrier medium and the biopsy needle or biopsy device by firstly bringing the carrier medium into physical contact with a tissue sample held by a sample part of the biopsy needle or biopsy device, and by secondly bringing the carrier medium away from the sample part of the biopsy needle or biopsy device.

The invention furthermore relates to a tissue collection device for collection of one or more tissue samples from a biopsy needle or biopsy device, the tissue collection device including a tissue sample positioning arrangement adapted to receive and/or support a biopsy needle or biopsy device holding a tissue sample, the tissue collection device including a carrier medium adapted to adhere to a tissue sample, the tissue collection device being adapted to perform a tissue collection operation by relative movement between the carrier medium and the biopsy needle or biopsy device by firstly bringing the carrier medium into physical contact with a tissue sample held by a sample part of the biopsy needle or biopsy device, and by secondly bringing the carrier medium away from the sample part of the biopsy needle or biopsy device.

In an embodiment, the tissue sample positioning arrangement is adapted to support a biopsy needle relative to a housing of the tissue collection device in a fixed position in a transverse direction of the biopsy needle, and the tissue collection device is adapted to perform the tissue collection operation by movement of the carrier medium in a transverse direction of the biopsy needle. Thereby, a controlled tissue collection operation may be achieved without risk of squeezing or deforming the tissue samples.

In an embodiment, the tissue collection device includes a sample storage with at least one sample compartment having the form of a channel in which the carrier medium is arranged.

In an embodiment, the carrier medium, preferably in the form of a sheet material, covers a bottom and two opposed sides of the channel forming the at least one sample compartment. Thereby, the tissue sample may be partly surrounded by the carrier medium and it may thereby be ensured that a sufficiently large contact area between the carrier medium and the tissue sample is achieved so that the tissue sample safely adheres to the carrier medium. Thereby, a more controlled and consistent tissue collection operation may be achieved without any risk that the tissue sample falls off from the carrier medium during the tissue collection operation.

In an embodiment, the carrier medium arranged in the channel is formed as a single piece which has been folded to form a bottom part connecting two opposed side parts, whereby the bottom part of the carrier medium covers the bottom of the channel and the respective side parts of the carrier medium cover the corresponding opposed sides of the channel. Thereby, each tissue sample may be collected on a separate single piece of carrier medium so that the tissue samples may easily be collected and subsequently distributed as required for examination.

In an embodiment, free edges of the respective side parts of the carrier medium are held in place in the channel by respective protrusions arranged at either side of the channel. Thereby, each single piece of carrier medium may be held safely in place in the channel during sampling and may subsequently easily be removed with the tissue sample adhered thereto.

In an embodiment, at least a central part of the bottom part of the carrier medium covering the bottom of the channel is bulged away from the bottom of the channel at least before bringing the carrier medium into physical contact with a tissue sample. Thereby, during the tissue collection operation, at least a central part of the bottom part of the carrier medium may deform somewhat, preferably elastically, when the carrier medium contacts the tissue sample. This may be advantageous in that the carrier medium may thereby better conform to the form of a tissue compartment of an inner needle of a biopsy needle. In some embodiments, such tissue compartment may have a form like a canoe in which the carrier medium, for instance in the form of biopsy paper or the like may fit by having a bulging and/or rounded form. Furthermore, it may be avoided that the tissue samples are squeezed or deformed by pressing the carrier medium too hard against the tissue sample. Furthermore, the preferably elastic deformation of the carrier medium may result in that the tissue sample adheres even better to the carrier medium due to the fact that the carrier medium contacts the tissue sample during a longer period of time during the tissue collection operation in a more gentle and controlled way with a more uniform pressure applied between the carrier medium and the tissue sample. The carrier medium may contact the tissue sample during a longer period of time during the tissue collection operation, because the carrier medium may contact the tissue sample during the period of deformation of the carrier medium as the carrier medium is moved in the direction against the tissue sample, as opposed to if the carrier medium just contacts the tissue sample from when the carrier medium finally reaches the tissue sample at the end of the movement of the carrier medium in the direction against the tissue sample and until the carrier medium is again removed from the sample needle or biopsy device by moving it in the opposite direction.

In an embodiment, the at least central part of the bottom part of the carrier medium covering the bottom of the channel has been preformed into the bulging configuration by stamping.

In an embodiment, the sample storage is configured as a drum, in which the sample compartments are arranged along the periphery of the drum, and the drum is arranged to be rotated a number of angular steps corresponding to the distance between two neighbouring sample compartments. For instance, each time a tissue sample has been collected, the drum may be rotated so many of said angular steps that the tissue sample is visible on the side of the drum which is opposed to the position of the biopsy needle. This may ensure that the user is able to see that the tissue sample is satisfactory, before continuing. For instance, each time a tissue sample has been collected, the drum may be rotated so many of said angular steps that correspond to approximately ½, ⅓ etc. of the total number of steps corresponding to an entire rotation of the drum.

In an embodiment, the tissue collection device is adapted to perform a tissue collection operation by displacement of the drum relative to the housing in the direction of the biopsy needle and back again when the drum has been rotated one or more angular steps.

In a structurally particularly advantageous embodiment, the drum is adapted to be displaced relative to the housing in the direction of the biopsy needle and back again by means of a crankshaft arranged internally in the drum.

In an embodiment, the crankshaft has a first and a second opposed end journaled in the housing and a crankpin offset from the axis of rotation of the crankshaft, and wherein the crankpin is arranged in a hub of the drum.

In an embodiment, the drum is journaled rotationally about the hub, the hub is fixed against rotation, and the crankpin is arranged in a first groove extending diametrically in the hub.

In an embodiment, the hub is fixed against rotation by means of the first end of the crankshaft which is arranged in a second groove extending diametrically in a first end piece of the hub at right angles to the first groove and by means of a pin of the hub arranged in a third groove extending in the housing in parallel with the second groove.

In an embodiment, the drum is adapted to be rotated in angular steps by means of spring-biased arm arranged pivotally in the housing at a first end thereof and having a second end adapted to engage a number of protrusions arranged at the periphery of the drum, and each protrusion corresponds to a sample compartment.

In an embodiment, one of the sample compartments does not have a corresponding one of said protrusions. Thereby, it may be avoided that more tissue samples are collected in the same sample compartment, because the drum will not be able to rotate further when said one of the sample compartments not having a corresponding protrusion is located at the position next to the biopsy needle or biopsy device.

In an embodiment, the drum preferably has a marking at its periphery being visible from outside the housing when said one of the compartments is at the position next to the biopsy needle or biopsy device. Thereby, a user of the device may be informed that all sample compartments have been filled up with corresponding tissue samples and that the drum should be replaced with another drum or the carrier medium arranged in the drum should be replaced with new carrier medium.

In an embodiment, the drum is prevented from rotation against a dedicated rotational direction by means of a ratchet mechanism. Thereby, a controlled rotation of the drum may be ensured.

In an aspect of the invention, it relates to a biopsy device comprising a tissue collection device as described above. Thereby, by integrating the tissue collection device in a biopsy device, the whole process of taking a number of tissue samples from a patient and collecting the tissue samples in the tissue collection device may be automated and thereby facilitated and improved by being more consistent.

In an embodiment of the invention, the tissue collection device collects one or more tissue samples from a biopsy needle of the biopsy device and saves the tissue samples within the biopsy device until the desired number of tissue samples are obtained from the target tissue.

In a particular advantageous embodiment, the biopsy device has a biopsy needle including an outer cutting needle and an inner needle with a tissue compartment for the tissue sample, the outer cutting needle surrounds the inner needle and is arranged slidingly along the inner needle, the outer cutting needle has a cutting end and a sample opening or sample end at a distance from the cutting end, the inner needle is slidable so that the tissue compartment is displaceable form the cutting end of the outer cutting needle to the sample opening or sample end of the outer cutting needle, and the tissue collection device is arranged at the sample opening or sample end of the outer cutting needle. Thereby, the outer cutting needle may be retained inserted in the tissue of the patient during the taking of more samples which may be particularly advantageous for instance when taking tissue samples from the prostate whereby the gut may otherwise be penetrated once for every tissue sample taken. Because the tissue sample is collected by the tissue collection device from the sample opening or sample end of the outer cutting needle which sample opening or sample end is located at an opposite end of the outer cutting needle in relation to the cutting end of the outer cutting needle, the cutting end of the outer cutting needle may remain inside the tissue of the patient during the taking of several tissue samples which are sequentially transported one by one longitudinally through the outer cutting needle by longitudinal displacement of the inner needle with a tissue sample located in the tissue compartment.

THE DRAWINGS

Figure 1B:
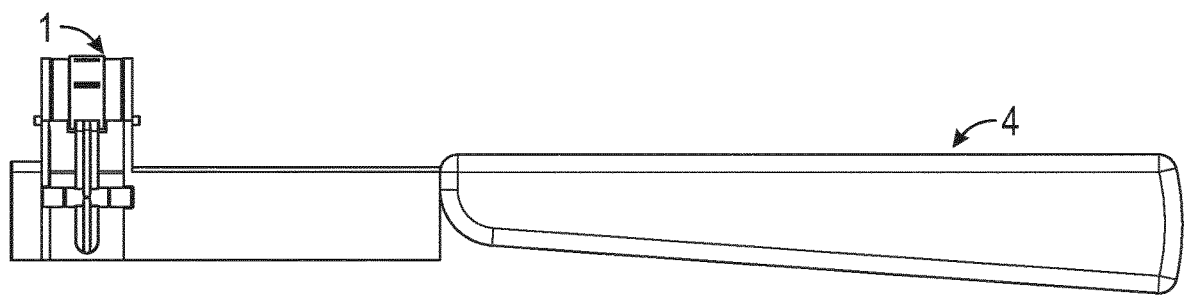
Figure 1A:
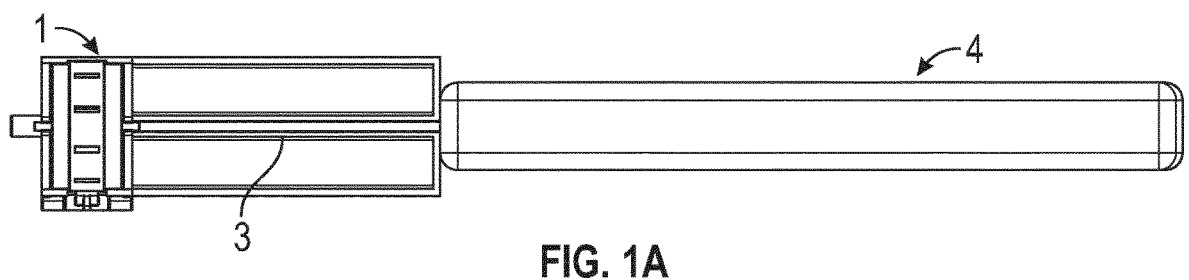
Figure 1F:
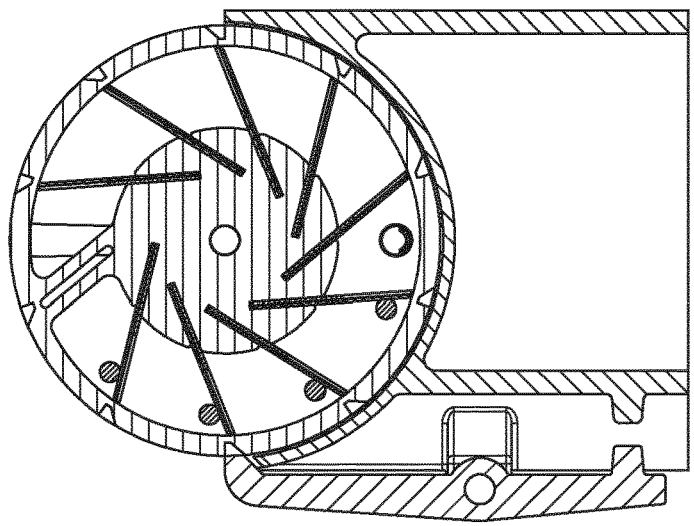
Figure 1E:
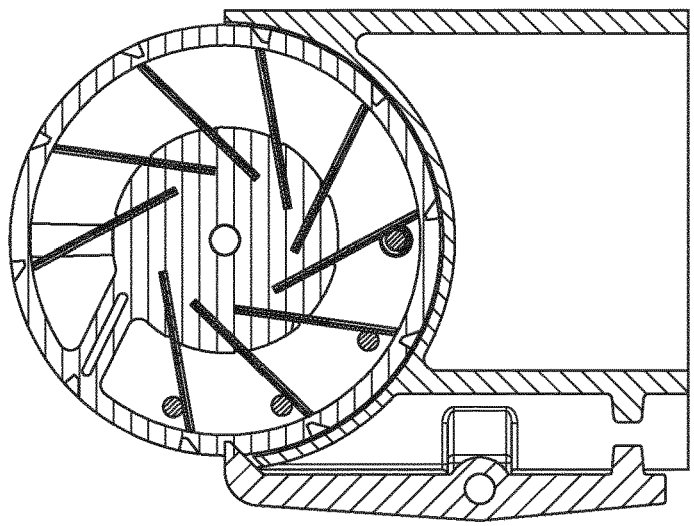
Figure 1D:
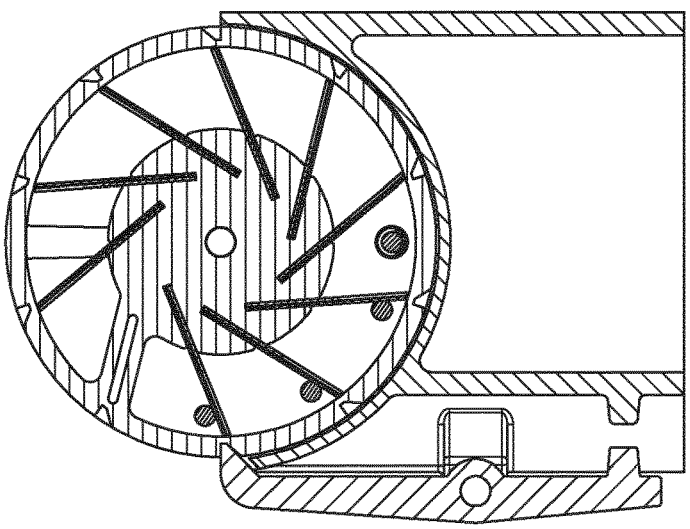
Figure 5:
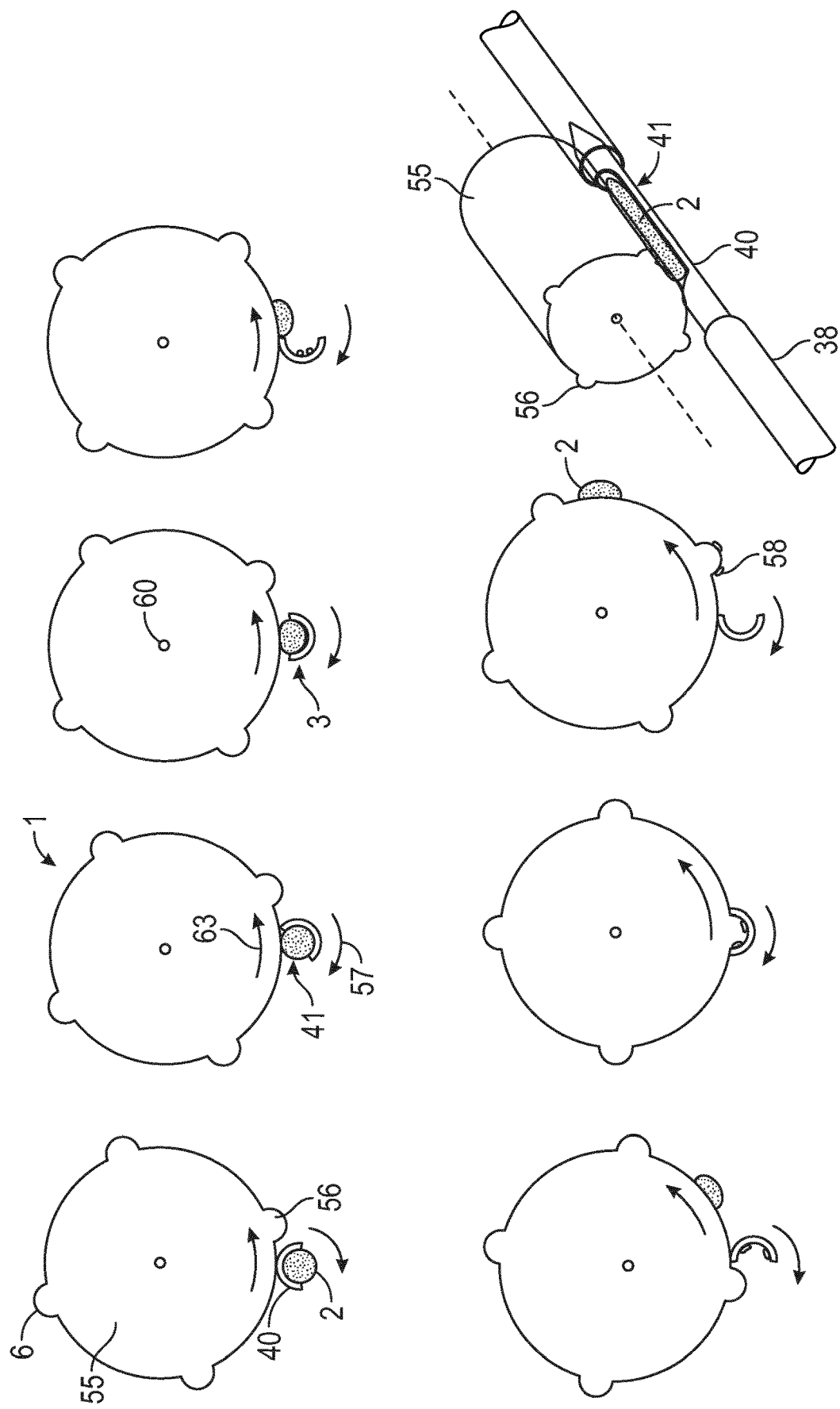
Figure 6:
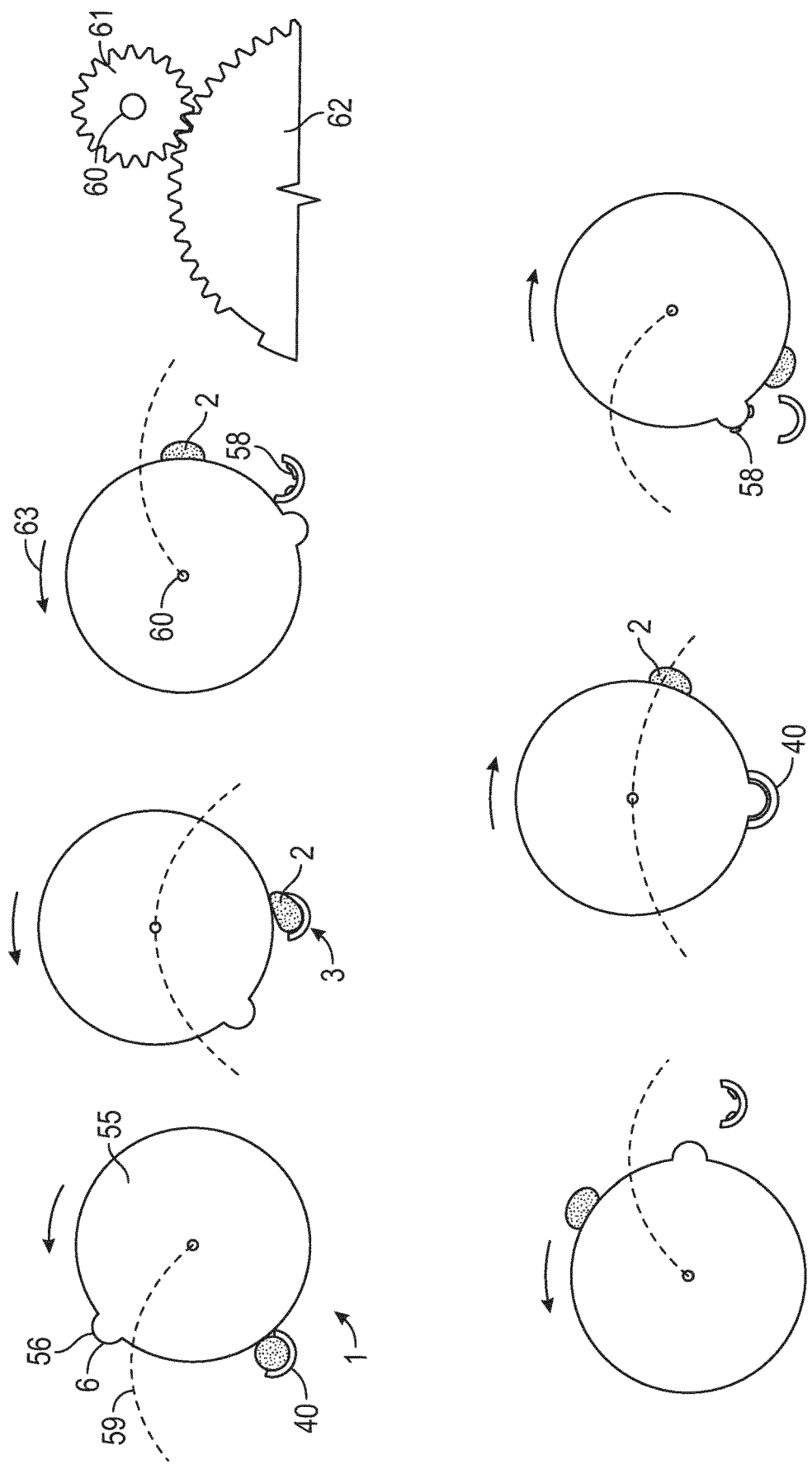
Figure 8:
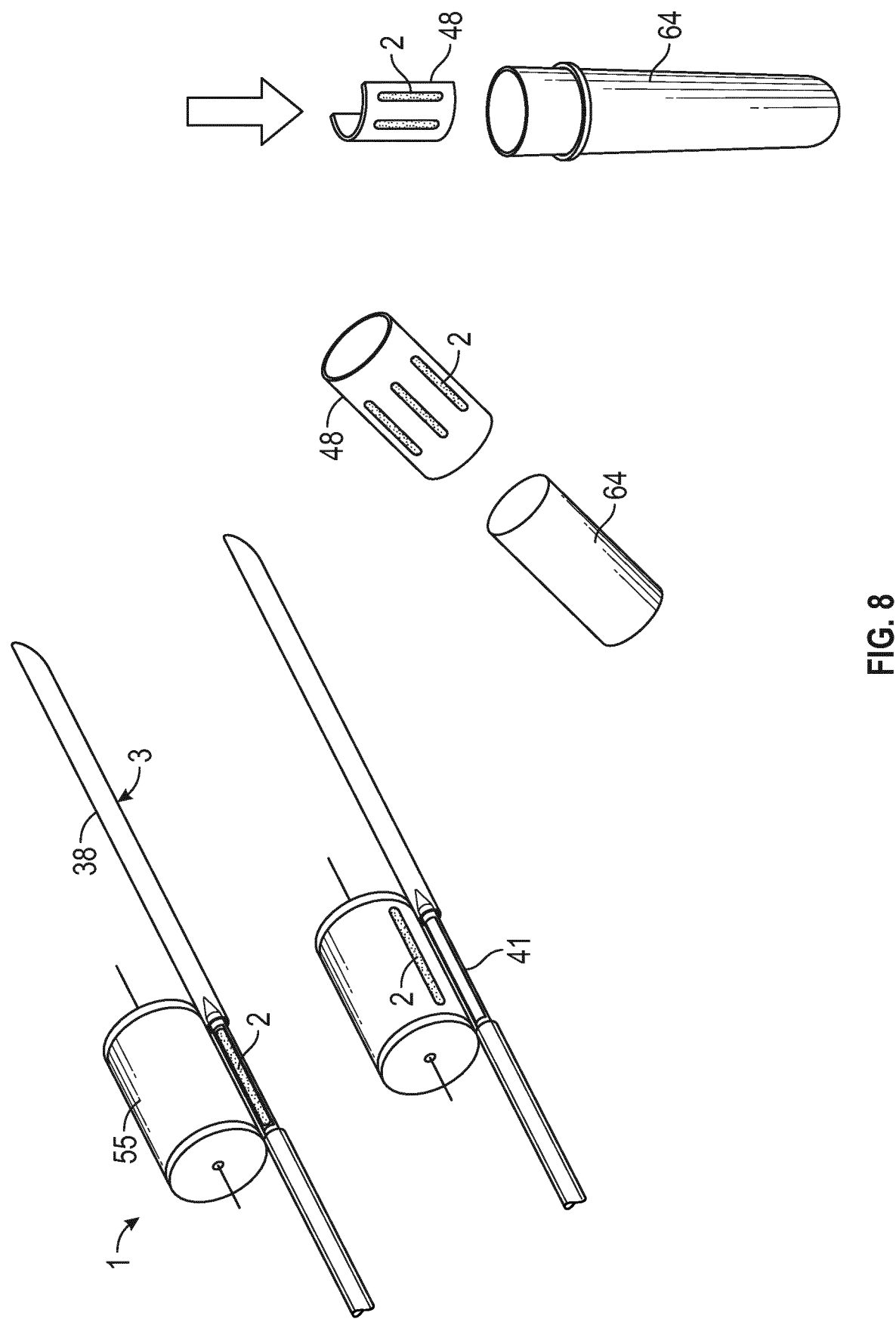
Figure 9:
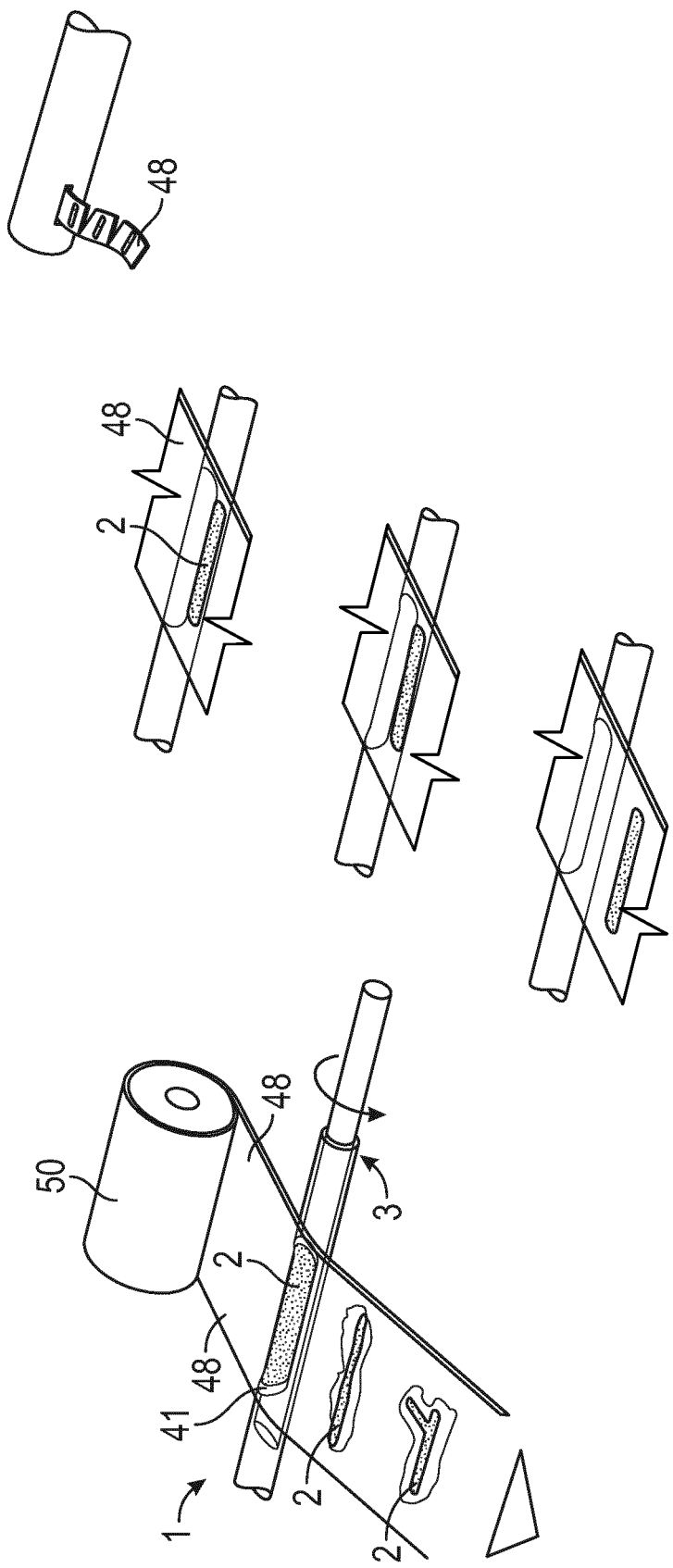
Figure 14:
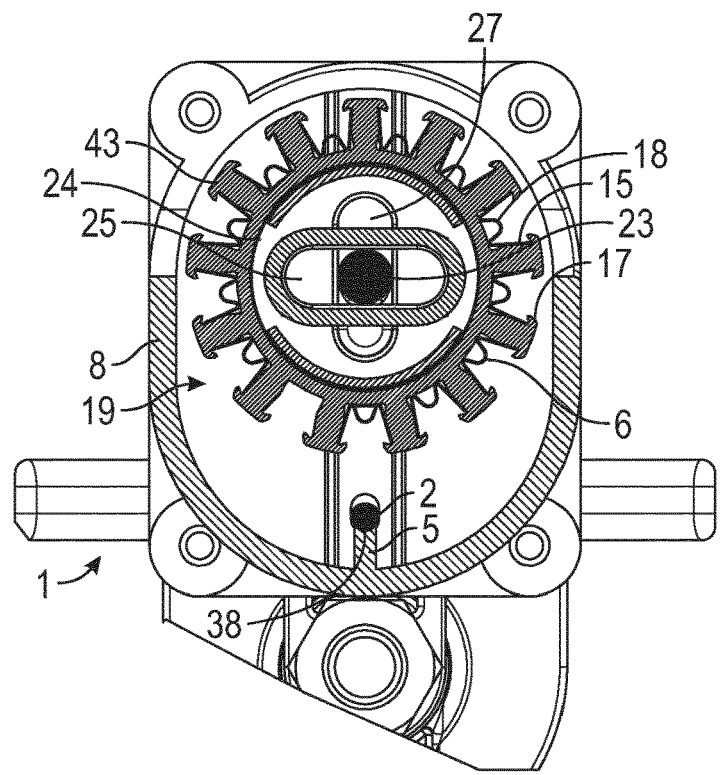
Figure 15:
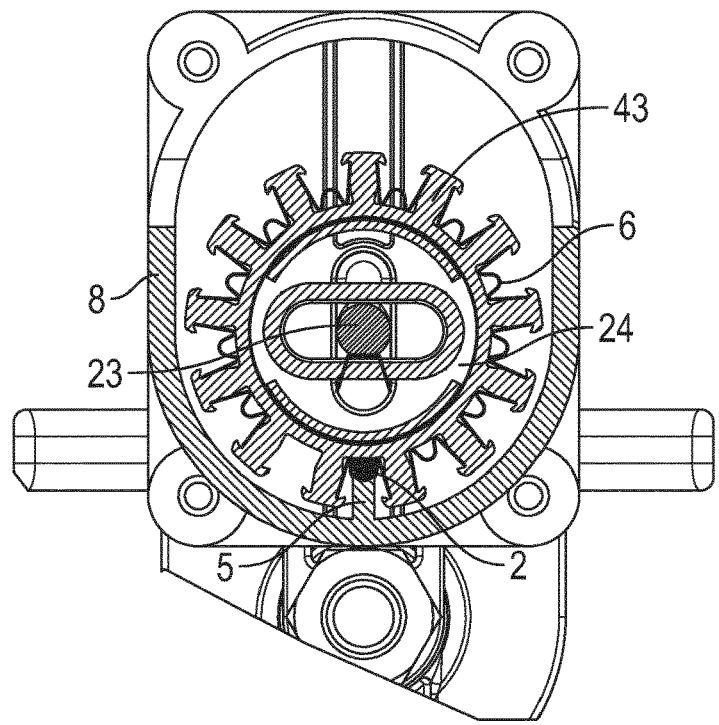
Figure 16B:
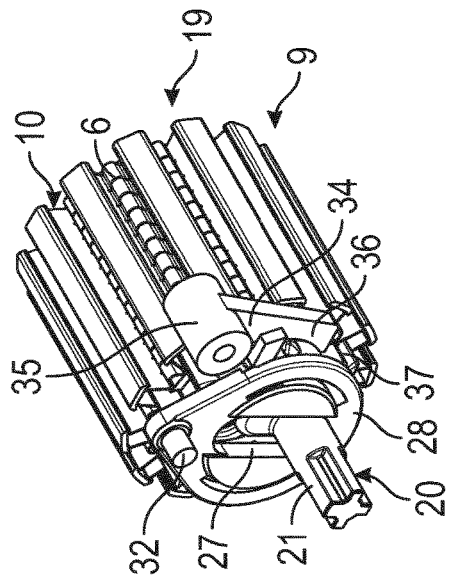
Figure 17B:
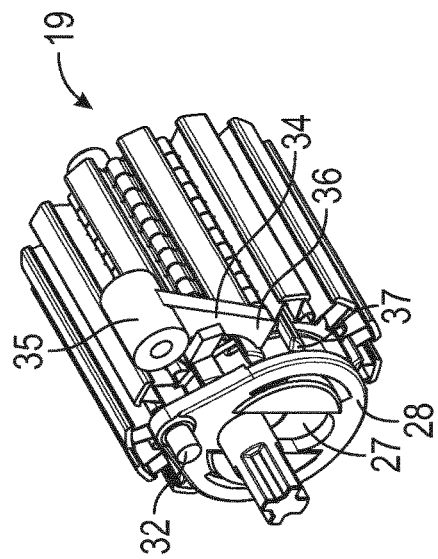
Figure 16A:
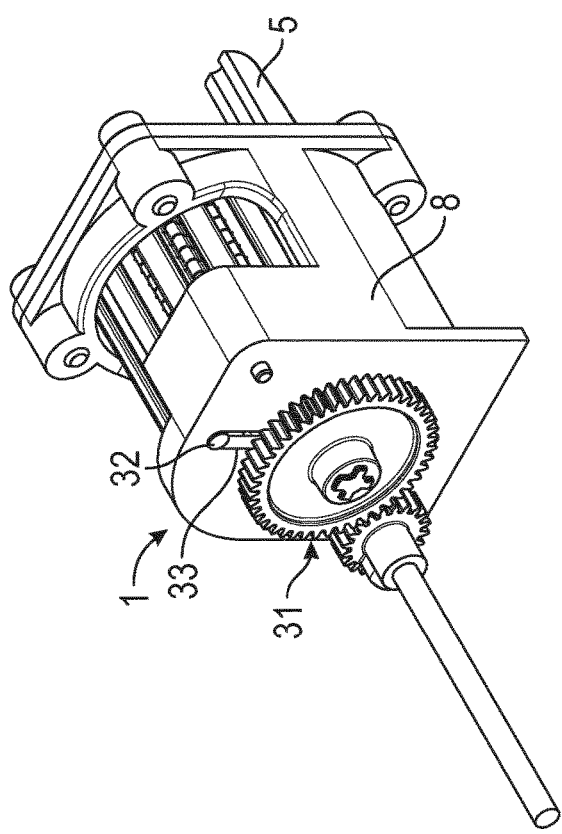
Figure 17A:
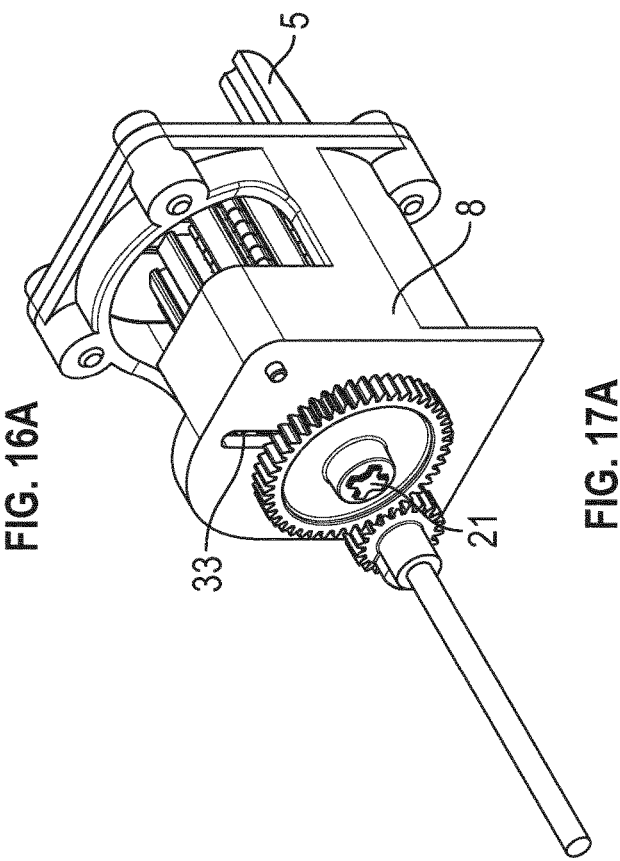
Figure 18:
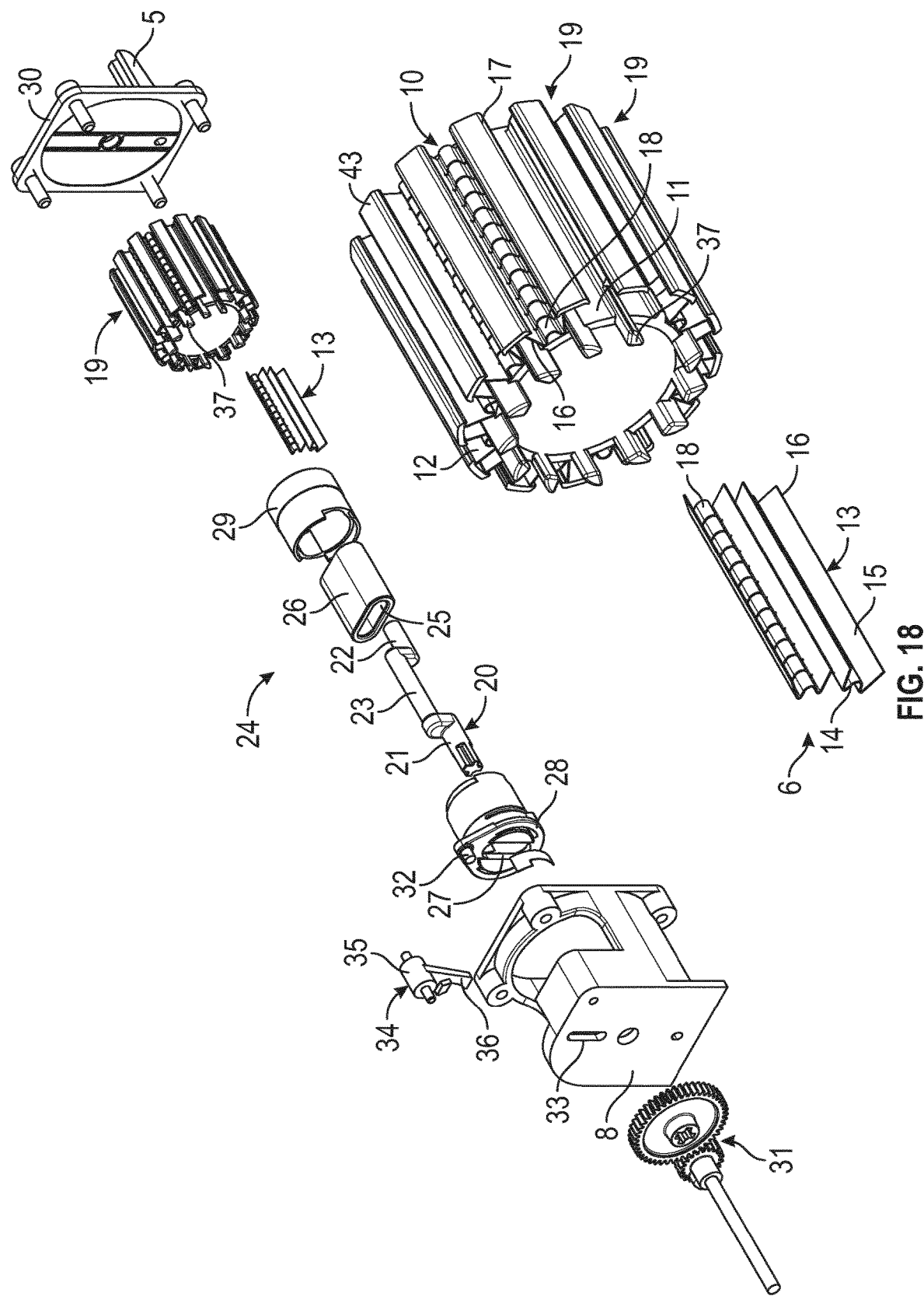
Figure 21A:
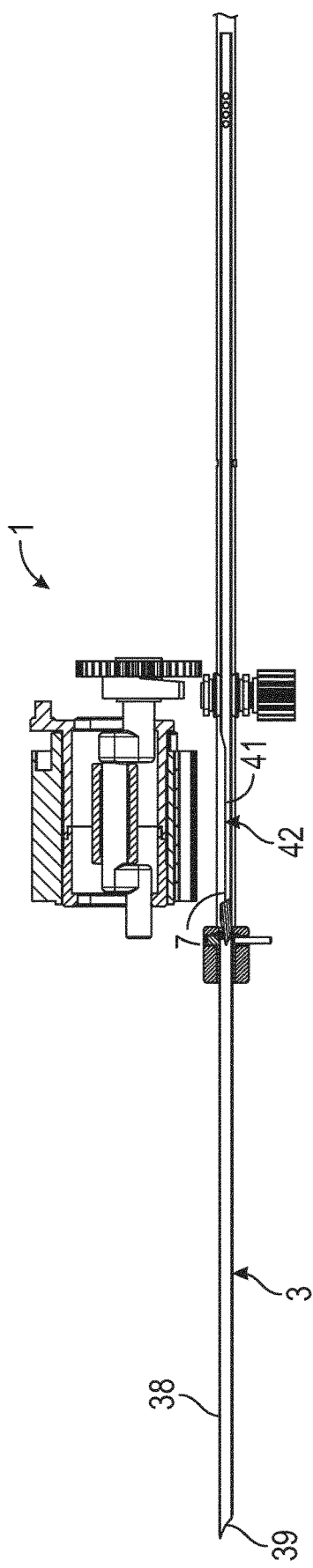
Figure 21B:
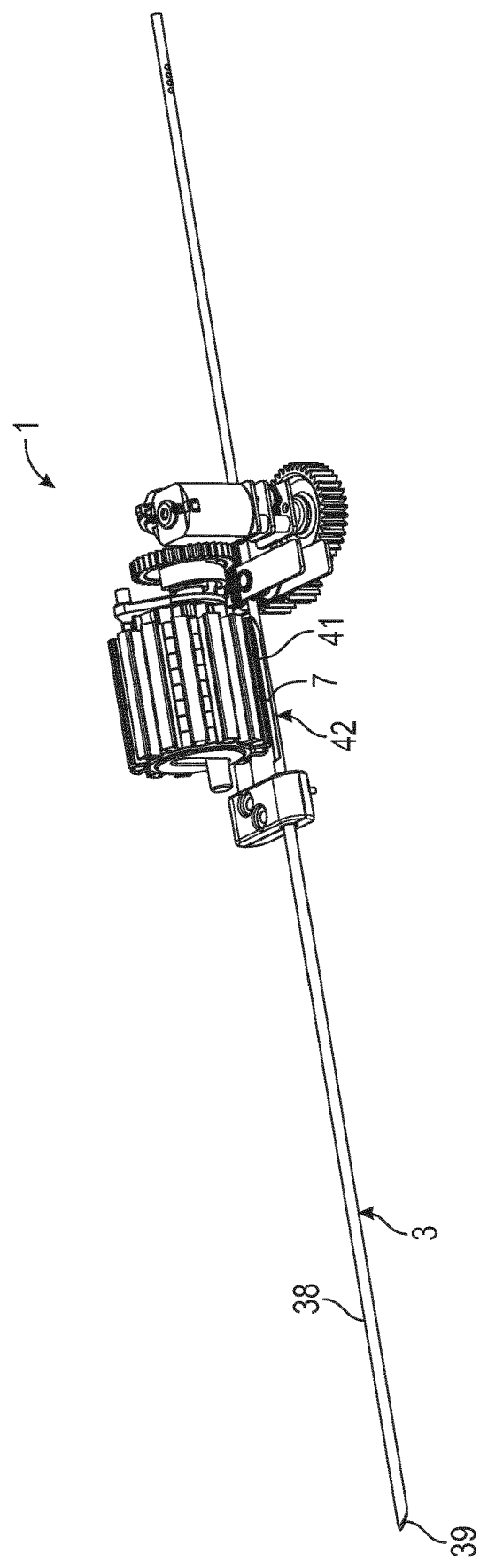

In the following, a few exemplary embodiments of the invention, are described in further detail with reference to the drawings, of which FIGS. 1A-1C illustrate schematically a top view, a side view and a cross-sectional view, respectively, of a tissue collection device according to a first embodiment of the invention, FIGS. 1D-1F illustrate schematically three steps of operation, respectively, of the tissue collection device shown in FIGS. 1A-1C, FIGS. 2A-2C illustrate schematically a top view, a side view and a cross-sectional view, respectively, of a tissue collection device according to a second embodiment of the invention, FIGS. 2D-2G illustrate schematically four steps of operation, respectively, of the tissue collection device shown in FIGS. 2A-2C, FIGS. 3A-3C illustrate schematically a top view, a side view and a cross-sectional view, respectively, of a tissue collection device according to a third embodiment of the invention, FIGS. 3D-3G illustrate schematically four steps of operation, respectively, of the tissue collection device shown in FIGS. 3A-3C, FIGS. 4A-4B illustrate schematically a perspective view and a cross-sectional view, respectively, of a biopsy device according to an embodiment of the invention, FIG. 5 illustrates schematically the function of a tissue collection device according to a fourth embodiment of the invention, FIG. 6 illustrates schematically the function of a tissue collection device according to a fifth embodiment of the invention, FIG. 7 illustrates schematically the function of a tissue collection device according to a sixth embodiment of the invention, FIG. 8 illustrates schematically the function of a tissue collection device according to a seventh embodiment of the invention, FIG. 9 illustrates schematically the function of a tissue collection device according to an eighth embodiment of the invention, FIG. 10 illustrates schematically the function of a tissue collection device according to a ninth embodiment of the invention, FIG. 11 illustrates schematically the function of a tissue collection device according to a tenth embodiment of the invention, FIG. 12A illustrates in a side view schematically a biopsy device interacting with a tissue collection device according to an eleventh embodiment of the invention, in a resting position of the tissue collection device, FIG. 12B illustrates in an enlarged view the tissue collection device of FIG. 12A, FIG. 12C illustrates a top view of the biopsy device and the tissue collection device of FIG. 12A, FIG. 12D illustrates a perspective view of the biopsy device and the tissue collection device of FIG. 12A, FIGS. 13A to 13D illustrate schematically views corresponding to the views of FIGS. 12A to 12D, respectively, in a sampling position of the tissue collection device, FIG. 14 illustrates schematically a cross-section through the tissue collection device in the resting position of FIG. 12A, taken along the line XIV-XIV of FIG. 12A, FIG. 15 illustrates schematically a cross-section corresponding to that of FIG. 14 through the tissue collection device in the sampling position of FIG. 13A, taken along the line XV-XV of FIG. 13A, FIG. 16A illustrates schematically a perspective view of the tissue collection device in the resting position of FIG. 12A, FIG. 16B illustrates schematically a perspective view of the drum of the tissue collection device in the resting position of FIG. 16A, FIG. 17A illustrates schematically a perspective view of the tissue collection device in the sampling position of FIG. 13A, FIG. 17B illustrate schematically a perspective view of the drum of the tissue collection device in the sampling position of FIG. 17A, FIG. 18 illustrates schematically a perspective exploded view of the tissue collection device of FIGS. 16 and 17, FIGS. 19A and 19B illustrate a cross-sectional view and a perspective view, respectively, of part of a biopsy device with integrated tissue collection device according to an embodiment of the invention, wherein the tissue compartment of the inner needle extends from the cutting end of the outer cutting needle, FIGS. 20A and 20B illustrate a cross-sectional view and a perspective view, respectively, corresponding to the views of FIGS. 19A and 19B, respectively, wherein the tissue compartment of the inner needle has been retracted from the cutting end of the outer cutting needle to a position inside the outer cutting needle next to the cutting end, and FIGS. 21A and 21B illustrate a cross-sectional view and a perspective view, respectively, corresponding to the views of FIGS. 19A and 19B, respectively, wherein the tissue compartment of the inner needle has been retracted from the cutting end of the outer cutting needle to a position at the sample opening of the outer cutting needle.

DETAILED DESCRIPTION OF THE INVENTION

In the following detailed description, corresponding elements are generally provided with the same reference numerals.

FIGS. 12 to 18 illustrate an embodiment of a tissue collection device 1 according to the present invention for collection of one or more tissue samples 2 from a biopsy needle 3 or biopsy device 4. The tissue collection device 1 includes a tissue sample positioning arrangement 5 adapted to receive and support a biopsy needle 3 holding a tissue sample 2. As seen particularly well in FIG. 17A, the tissue sample positioning arrangement 5 of this embodiment has the form of a partly and upwards open sleeve in which the biopsy needle 3 may be inserted and subsequently supported during a tissue collection operation.

The tissue collection device 1 includes a carrier medium 6 adapted to adhere to a tissue sample 2 and is adapted to perform a tissue collection operation by relative movement between the carrier medium 6 and the biopsy needle 3 by firstly bringing the carrier medium 6 into physical contact with a tissue sample 2 held by a sample part 7 of the biopsy needle 3, and by secondly bringing the carrier medium 6 away from the sample part 7 of the biopsy needle or biopsy device as will be explained in further detail below.

As seen for instance in FIGS. 12A and 12B, the tissue sample positioning arrangement 5 is adapted to support a biopsy needle 3 relative to a housing 8 of the tissue collection device 1 in a fixed position in a transverse direction of the biopsy needle 3, and the tissue collection device 1 is adapted to perform the tissue collection operation by movement of the carrier medium 6 in a transverse direction of the biopsy needle 3. In FIGS. 12A and 12B, said transverse direction of the biopsy needle 3 is a vertical direction.

As particularly well seen in FIGS. 14 to 17, the tissue collection device 1 includes a sample storage 9 in the form of a drum 19 with a number of sample compartments 10 each having the form of a channel in which the carrier medium 6 is arranged. The carrier medium 6 has the form of a sheet material covering a bottom 11 and two opposed sides 12 of the channel forming the at least one sample compartment 10. The sheet material arranged in the channel is formed as a single sheet 13 which has been folded to form a bottom part 14 connecting two opposed side parts 15, whereby the bottom part 14 of the sheet material covers the bottom 11 of the channel and the respective side parts 15 of the sheet material cover the corresponding opposed sides 12 of the channel.

As particularly well seen in FIGS. 14 and 15, free edges 16 of the respective side parts 15 of the sheet material 13 are held in place in the channel by respective protrusions 17 arranged at either side 12 of the channel. A central part 18 of the bottom part 14 of the sheet material 13 covering the bottom 11 of the channel is bulged away from the bottom 11 of the channel at least be-fore bringing the sheet material into physical contact with a tissue sample 2. The central part 18 of the bottom part 14 may be preformed into the bulging configuration by stamping.

As further illustrated in FIGS. 12 to 17, the sample compartments 10 are arranged along the periphery of the drum, and the drum 19 is arranged to be rotated in angular steps corresponding to the distance between two neighbouring sample compartments 10. The tissue collection device 1 is adapted to perform a tissue collection operation by displacement of the drum 19 relative to the housing 8 in the direction of the biopsy needle 3 and back again when the drum has been rotated one angular step. In FIGS. 12A and 12B, and FIGS. 13A and 13B, said direction of the biopsy needle 3 and back again is a vertical direction. However, the tissue collection device 1 could just as well be mounted to a side of the biopsy needle 3, so that said direction of the biopsy needle 3 would be a horizontal direction in those figures.

As best understood when comparing FIGS. 16 and 17 with FIG. 18, the drum 19 is adapted to be displaced relative to the housing 8 in the direction of the biopsy needle 3 and back again by means of a crankshaft 20 arranged internally in the drum 19. The crankshaft 20 has first and second opposed ends 21, 22 journaled in the housing 8 and a crankpin 23 offset from the axis of rotation of the crankshaft 20, and the crankpin 23 is arranged in a hub 24 of the drum 19. The drum 19 is journaled rotationally about the hub 24, and the hub is fixed against rotation. The crankpin 23 is arranged in a first groove 25 extending diametrically in the hub 24. The hub 24 is fixed against rotation by means of the first end 21 of the crankshaft 20 which is arranged in a second groove 27 extending diametrically in a first end piece 28 of the hub 24 at right angles to the first groove 25 and by means of a pin 32 of the hub arranged in a third groove 33 extending in the housing 8 in parallel with the second groove 27.

As particularly well seen in FIGS. 16B and 17B, the drum 19 is adapted to be rotated in angular steps by means of spring-biased arm 34 arranged pivotally in the housing 8 at a first end 35 thereof and having a second end 36 adapted to engage a number of protrusions 37 arranged at the periphery of the drum 19. Each protrusion 37 corresponds to a sample compartment 10. The arm 34 is spring-biased into engagement with the protrusions 37 by means of a not shown spring. As seen, when the drum 19 is displaced away from the biopsy needle 3, i.e. the upward direction in FIGS. 16B and 17B, the second end 36 of the spring-biased arm 34 presses on a first face of a protrusion 37. Thereby, the drum 19 is rotated one step. The first face extends at least substantially radially in relation to the drum. On the other hand, when the drum 19 is displaced in the opposite direction of the biopsy needle 3, i.e. in the downward direction in FIGS. 16B and 17B, the second end 36 of the spring-biased arm 34 slides over a second face of said protrusion 37 so that the drum 19 is not rotated. Said second face is oblique in relation to the first face.

As noted in FIG. 18, one of the sample compartments 10 does not have a corresponding one of said protrusions 37. Thereby it is achieved that a user of the device may be informed that all sample compartments 10 have been filled up with corresponding tissue samples 2 and that the drum 19 should be replaced with another drum or the carrier medium 6 arranged in the drum 19 should be replaced with new carrier medium. Furthermore, the drum 19 is provided with a marking at its periphery being visible to the user from outside the housing 8 when said one of the compartments 10 is at the position next to the biopsy needle 3. Said marking is not visible in the figures, but may for instance be a red marking on a part of the drum 19, such as a wall 43 between the channels forming the sample compartments 10. A window may be provided in the wall of the housing 8 at a corresponding position, so that the marking is visible from outside the housing 8 when said one of the compartments 10 is at the position next to the biopsy needle 3. The drum 19 is further prevented from rotation against a the dedicated rotational direction by means of a not shown ratchet mechanism. The dedicated rotational direction in FIGS. 16B and 17B is clockwise.

FIGS. 19 to 21 illustrate a part of a biopsy device 4 with integrated tissue collection device 1 according to an embodiment of the invention. The tissue collection device 1 corresponds to the embodiment illustrated in FIGS. 14 to 18; however, the housing 8 of the tissue collection device 1 may be integrated or arranged in a not shown housing of the biopsy device 4. As seen, generally only the biopsy needle 3 of the biopsy device 4 is illustrated in these figures. However, it is to be understood that the tissue collection device 1 is mounted in said not shown housing of the biopsy device 4 at the illustrated position in relation to the biopsy needle 3 in order to collect tissue samples from a sample opening 42 or sample end of the biopsy needle 3 at a distance from a cutting end 39 of the biopsy needle 3, as will be explained in further detail below.

As seen, the biopsy device illustrated in FIGS. 19 to 21 has a biopsy needle 3 including an outer cutting needle 38 and an inner needle 40 with a tissue compartment 42 for the tissue sample 2. The outer cutting needle 38 surrounds the inner needle 40 and is arranged slidingly along the inner needle. The outer cutting needle 38 has a cutting end 39 and a sample opening 42 or sample end at a distance from the cutting end 39. The inner needle 40 is slidable so that the tissue compartment 41 is displaceable form the cutting end 39 of the outer cutting needle 38 to the sample opening 42 or sample end of the outer cutting needle 38. The tissue collection device 1 is arranged at the sample opening 42 or sample end of the outer cutting needle 38.

In FIGS. 19A and 19B, the tissue compartment 41 of the inner needle 40 extends from the cutting end 39 of the outer cutting needle 38, so that a tissue sample 2 may enter the tissue compartment 41 when the biopsy needle 3 is placed in the tissue of a patient. In FIGS. 20A and 20B, the tissue compartment 41 of the inner needle 40 has been retracted from the cutting end 39 of the outer cutting needle 38 to a position inside the outer cutting needle next to the cutting end. This position is appropriate for insertion of the biopsy needle 3 into the tissue of a patient. In FIGS. 21A and 21B, the tissue compartment 41 of the inner needle 40 has been retracted from the cutting end 39 of the outer cutting needle 38 to a position at the sample opening 42 of the outer cutting needle 38. In this position, a tissue sample 2 may be collected from the tissue compartment 41 of the inner needle 40 by means of the tissue collection device 1 as explained above, and this may be done when the outer cutting needle 38 is still placed in the tissue of a patient. Thereby, more tissue samples 2 may be collected by only penetrating the patient once. This may be particularly advantageous for instance when taking tissue samples from the prostate whereby the gut may otherwise be penetrated once for every tissue sample taken.

In an embodiment of the invention, the carrier medium includes a liquid absorbing material. Thereby, because a tissue sample typically has a high content of fluid, it may be ensured that the tissue sample may adhere to the carrier medium.

In an embodiment of the invention, the carrier medium has a porous sample contacting surface. Thereby, because a tissue sample typically has a high content of fluid, it may be ensured that the tissue sample may adhere to the carrier medium.

Other carrier mediums, which are capable of making tissue samples adhere to them, may also be used, such as sponges, cloth, felt leather, metal, glass, plastic materials or combinations thereof.

FIGS. 1A to 1F illustrate an embodiment of a tissue collection device 1 and a biopsy device 4, wherein the sample storage 9 is configured as a wheel or drum 19, in which the sample compartments 10 are arranged along the periphery of the wheel or drum 19. The sample compartments 10 are separated by pieces of carrier medium 44, each of which is fastened in the side 45 closest to the centre of the sample storage 9 only and is optionally supported by a piece 46 of a more rigid but still resilient supporting material. The sample storage 9 is arranged to be rotated in angular steps corresponding to the distance between two neighbouring sample compartments 10 in such a way that, when the part 41 of a biopsy needle 3 holding a tissue sample 2 is inserted in a direction parallel to the rotational axis 47 of the sample storage 9 into an empty sample compartment 10 thereof and the sample storage 9 is rotated one step, a piece of carrier medium 6 separating the sample compartment 10 in question and a neighbouring sample compartment 10 will be drawn across the biopsy needle 3, the tissue sample 2 in the biopsy needle 3 adheres to the piece of carrier medium 6 and follows it, as it passes the biopsy needle 3, leaving the biopsy needle 3 empty in the neighbouring empty sample compartment 10. It is understood that the tissue collection device 1 includes a not shown tissue sample positioning arrangement 5 adapted to receive and/or support the biopsy needle 3 or the biopsy device 4 holding a tissue sample 2. The tissue sample positioning arrangement 5 may in this embodiment be seen as the connection between tissue collection device 1 and the biopsy device 4. FIGS. 1D to 1F illustrate the different steps of operation of the tissue sampling device 1.

FIGS. 2A to 2G illustrate an embodiment of a tissue collection device 1 and a biopsy device 4 corresponding somewhat to the embodiment illustrated in FIGS. 12 and 13 described above. Each of the sample compartments 10 is open through the periphery of the sample storage 9 and lined with a piece of carrier medium 6, and the sample storage 9 is arranged to be rotated in angular steps corresponding to the distance between two neighbouring sample compartments 10 and to be able to move forth and back in a given radial direction in such a way that, when the part 41 of a biopsy needle 3 holding a tissue sample 2 is arranged adjacent an empty sample compartment 10 of the sample storage 9 in the radial direction in which the sample storage 9 is able to move forth and back, the sample storage 9 can move towards the biopsy needle 3 so that the empty sample compartment 10 surrounds the biopsy needle 3 and the tissue sample 2 therein, the tissue sample 2 in the biopsy needle 3 adheres to the piece of carrier medium 6 and follows it, when the sample storage 9 moves back and away from the biopsy needle 3 again, before it rotates one step to place a new empty sample compartment 10 in the position corresponding to the radial direction in which it can move forth and back. As seen the tissue collection device 1 includes a tissue sample positioning arrangement 5 adapted to receive and/or support the biopsy needle 3 holding a tissue sample 2. The tissue sample positioning arrangement 5 may in this embodiment be seen as the connection between tissue collection device 1 and the biopsy device 4. FIGS. 2D to 2G illustrate the different steps of operation of the tissue sampling device 1.

Figure 2C:
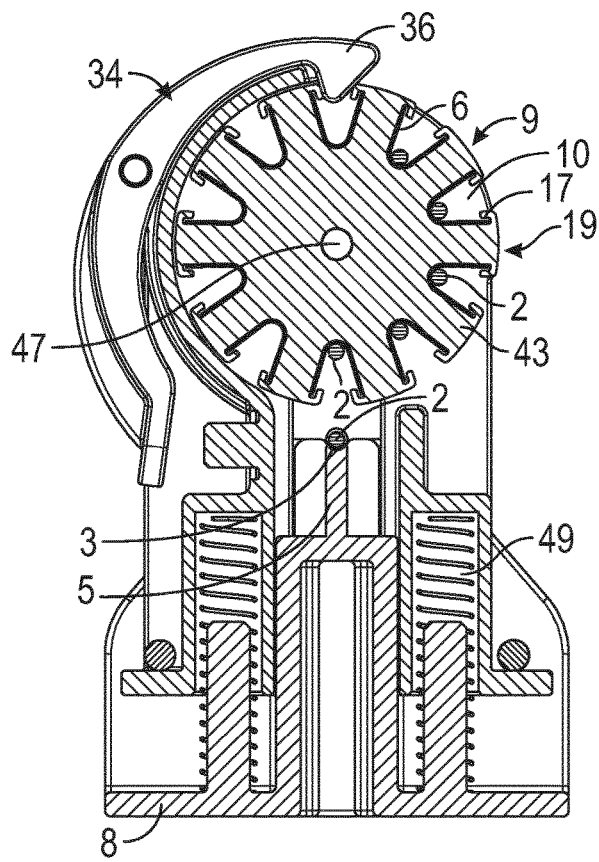
Figure 2B:
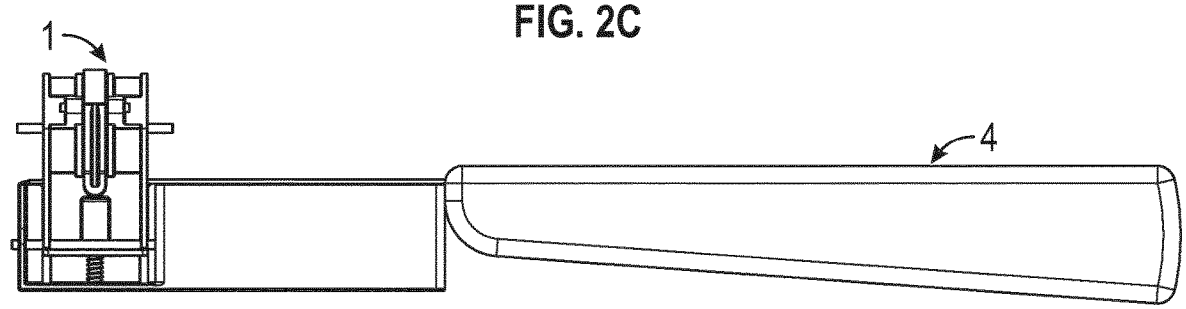
Figure 2A:
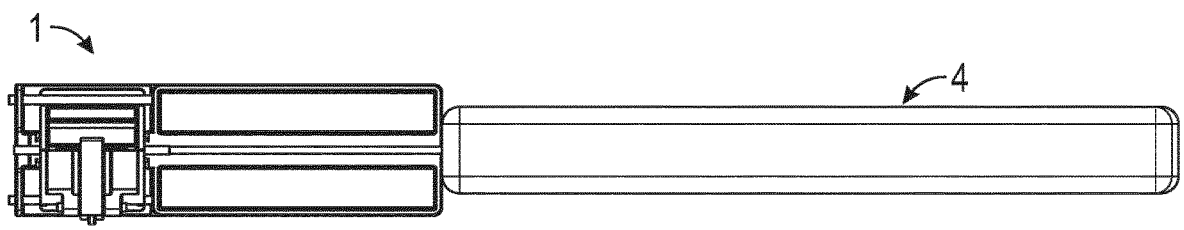
Figure 2D:
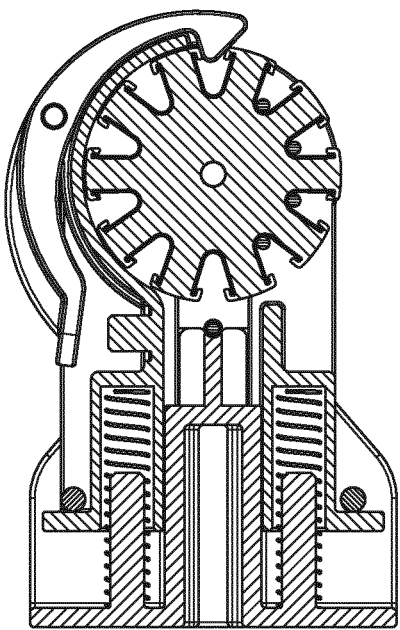
Figure 2E:
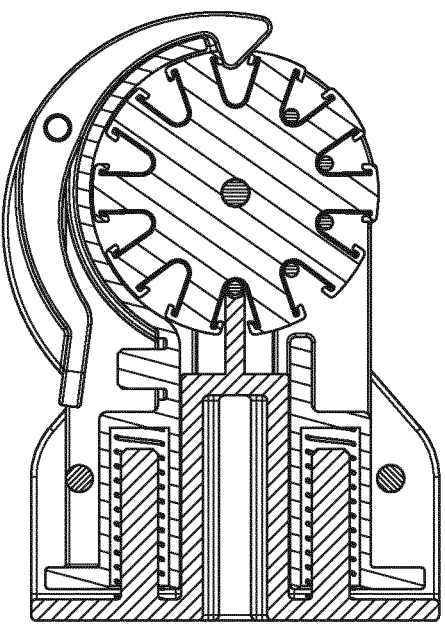
Figure 2F:
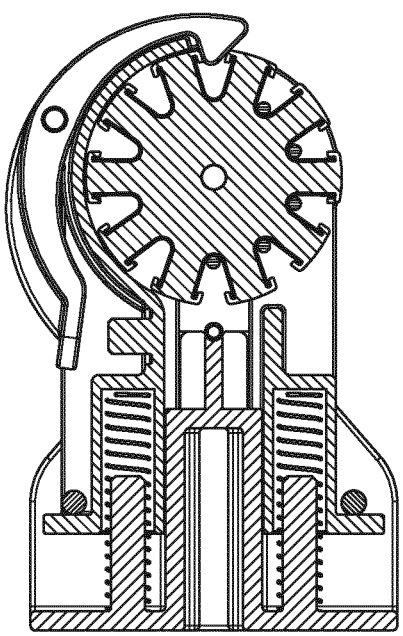
Figure 2G:
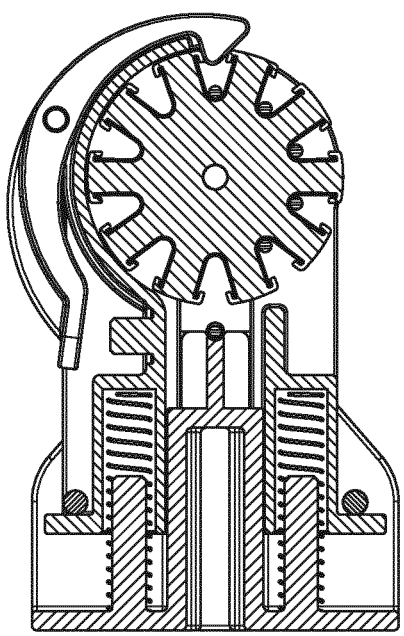
Figure 3C:
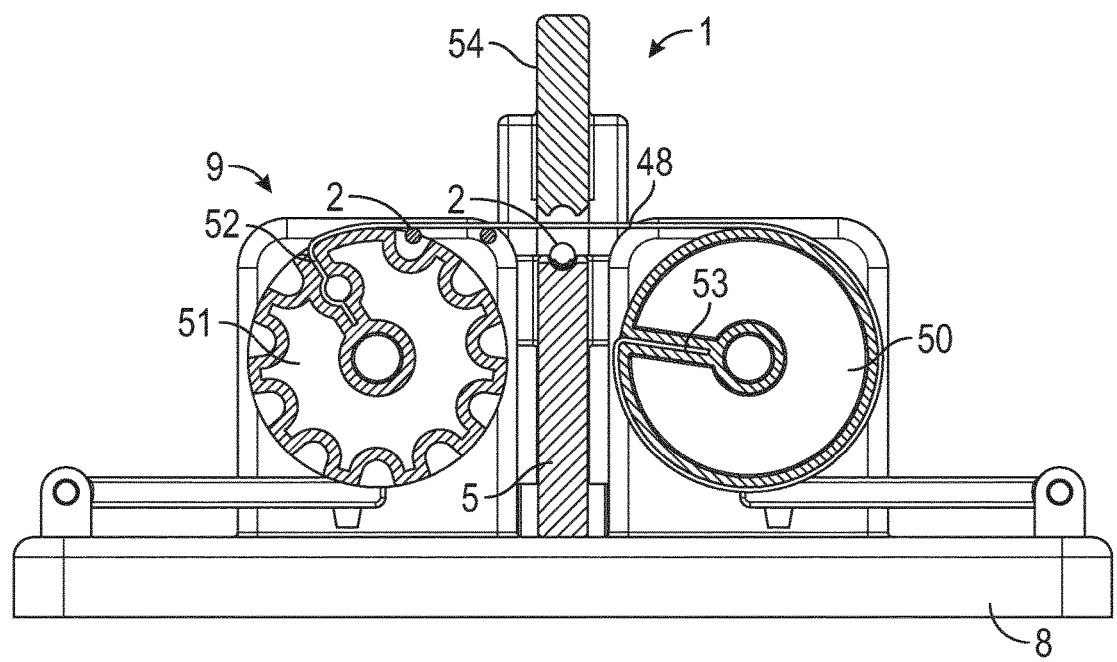
Figure 3B:
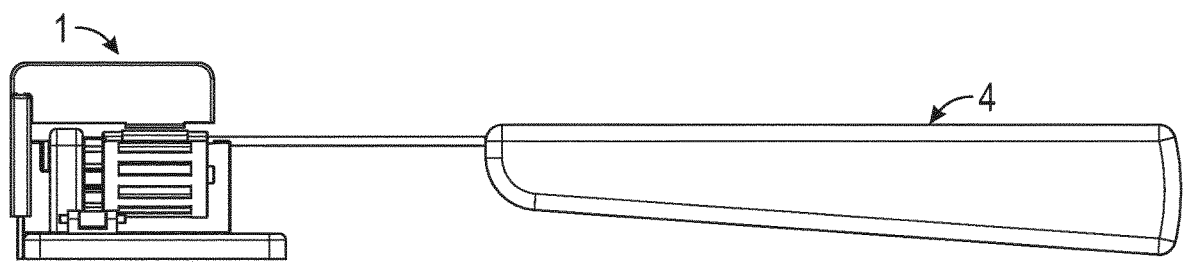
Figure 3A:
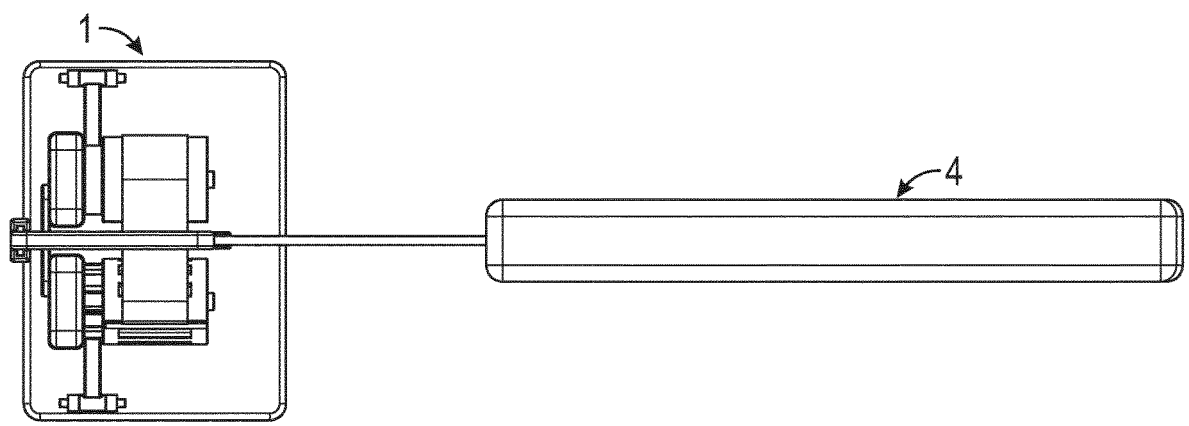
Figure 3D:
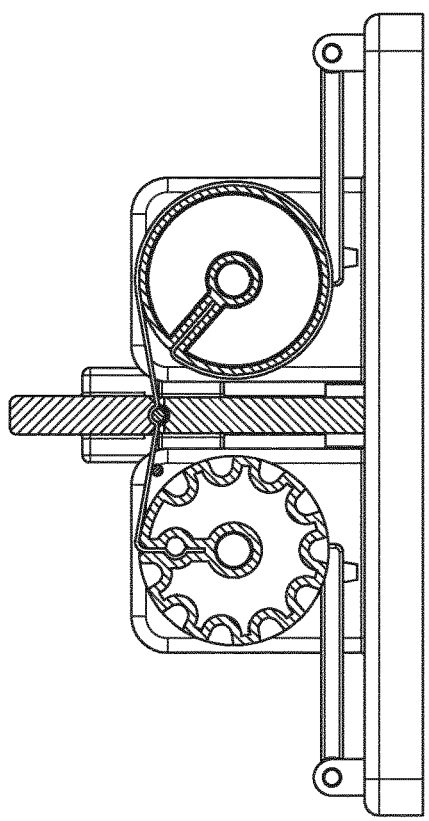
Figure 3F:
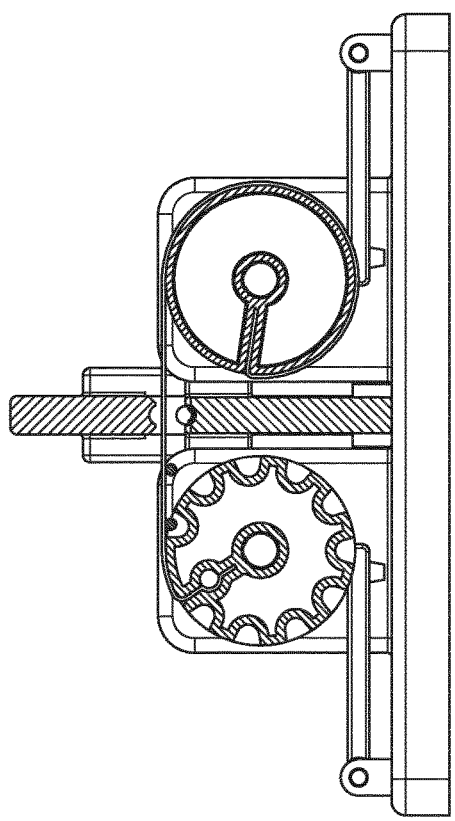
Figure 3E:
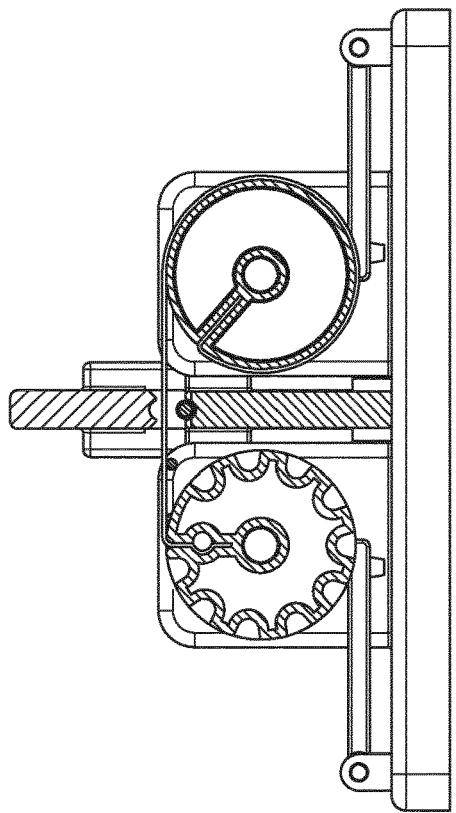
Figure 3G:
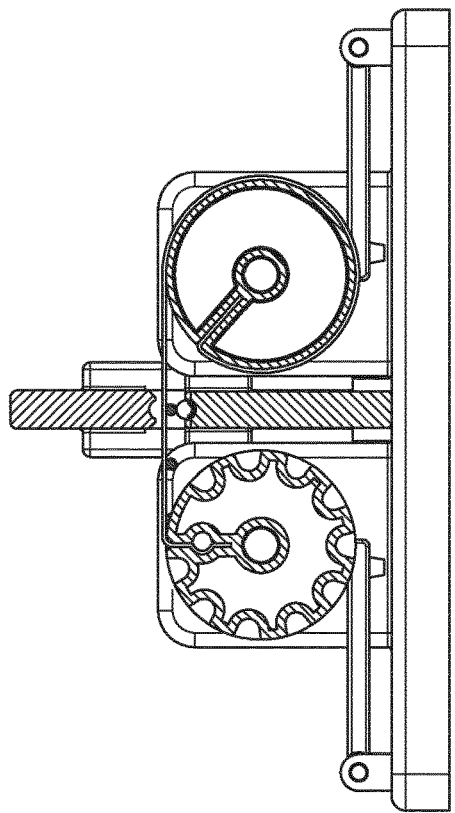

FIGS. 3A to 3G illustrate an embodiment of a tissue collection device 1 and a biopsy device 4, wherein the tissue collection device 1 is arranged to, by means of a sample piston 54, press temporarily a piece of carrier medium 6 against a tissue sample 2 within a biopsy needle 3 or biopsy device 4, whereby the tissue sample 2 adheres to the carrier medium 6 and is lifted away from the biopsy needle 3 or biopsy device 4 by the carrier medium 6, when the pressure onto the carrier medium 6 is released by the sample piston 54. As seen, in this embodiment, a single piece 48 of carrier medium 6 is arranged to collect a plurality of tissue samples 2, by being moved stepwise in a direction between successive collections of a tissue sample 2 from the same or a different biopsy needle 3 or biopsy device 4. As seen, in the illustrated embodiment, the tissue samples 2 are moved stepwise on the single piece 48 of carrier medium 6 which is unrolled from a first drum 50 of the tissue collection device 1 and subsequently rolled onto a second drum 51 of the tissue collection device 1. As seen, the tissue collection device 1 includes a tissue sample positioning arrangement 5 adapted to receive and/or support the biopsy needle 3 holding a tissue sample 2. FIGS. 3D to 2G illustrate the different steps of operation of the tissue sampling device 1.

FIGS. 4A and 4B illustrate an embodiment according to the invention of a biopsy device 4 with integrated tissue collection device 1. It is understood that the tissue collection device 1 includes a not shown tissue sample positioning arrangement 5 adapted to receive and/or support the biopsy needle 3 or the biopsy device 4 holding a tissue sample 2. The tissue sample positioning arrangement 5 may in this embodiment be seen as the connection between tissue collection device 1 and the biopsy device 4.

FIGS. 5 and 6 illustrate embodiments of a tissue collection device 1 being arranged to press a piece of carrier medium 6 into the biopsy needle 3 or biopsy device 4 after having removed the tissue sample 2 therefrom for cleansing the biopsy needle 3 or biopsy device 4 by sucking up any remaining tissue 58 therein. The carrier medium 6 included by the tissue collection device 1 is adapted to adhere to a tissue sample 2. As seen, a sample roller 55 is provided with sampling extensions 56 along its periphery in order to take up tissue samples 2 from a biopsy needle 3 in that the sampling extensions 56 extend into the tissue compartment 41 of the inner needle. During sampling, the inner needle 40 rolls on the sample roller 55 in the direction 57 when the sample roller 55 rolls in the direction 63. FIG. 6 illustrates an embodiment in which a shaft 60 of sample roller 55 follows a trajectory 59 during sampling whereby the sample roller 55 is so to say rolled on the biopsy needle 3. This is achieved by the illustrated arrangement of a cogwheel 61 on the shaft of the sample roller 55 and a cogwheel 62 in engagement with the cogwheel 61 on the shaft of sample roller.

FIG. 7 illustrates an embodiment in which a tissue collection device 1 is integrated into a biopsy device 4. As seen, a single piece 48 of carrier medium 6 is arranged to collect a plurality of tissue samples 2.

FIG. 8 illustrate an embodiment somewhat resembling the embodiment illustrated in FIGS. 5 and 6 in which a sample roller 55 is adapted to roll against a biopsy needle 3 in order to collect tissue samples 2. However, in this embodiment, the entire periphery of the sample roller 55 is covered by a single piece 48 of carrier medium 6 is arranged to collect a plurality of tissue samples 2. Subsequently to collecting tissue samples 2, the single piece 48 of carrier medium 6 may be stored in a sample container 64.

FIG. 9 illustrate an embodiment somewhat resembling the embodiment illustrated in FIGS. 3A to 3G in which tissue samples 2 are collected on a roll of a single piece 48 of carrier medium 6. FIG. 10 illustrate an embodiment somewhat resembling the embodiment illustrated in FIG. 7. In this embodiment, the tissue samples 2 are collected on a disc of a single piece 48 of carrier medium 6.

FIG. 11 illustrate an embodiment somewhat resembling a combination of the embodiments illustrated in FIGS. 3, 4, 8 and 9. In this embodiment, a biopsy device 4 with integrated tissue collection device 1 collects tissue samples 2 on a single piece 48 of carrier medium 6 in the form of a strip arranged on a wheel.

LIST OF REFERENCE NUMERALS 1 tissue collection device
2 tissue sample
3 biopsy needle
4 biopsy device
5 tissue sample positioning arrangement
6 carrier medium
7 sample part
8 housing of tissue collection device
9 sample storage
10 sample compartment in the form of channel
11 bottom of sample compartment
12 side of sample compartment
13 single sheet forming carrier medium
14 bottom part of single sheet of sheet material forming carrier medium
15 side part of single sheet
16 free edges
17 protrusions of channel
18 central part of bottom part of sheet material
19 drum
20 crankshaft
21 first end of crankshaft
22 second end of crankshaft
23 crankpin
24 hub
25 first groove in hub
26 groove-forming part
27 second groove in end piece of hub
28 first end piece of hub
29 second end piece of hub
30 end piece of housing
31 drive mechanism for crankshaft
32 pin of hub
33 third groove in housing
34 spring-biased arm
35 first end of spring-biased arm
36 second end of spring-biased arm
37 protrusion at periphery of drum
38 outer cutting needle
39 cutting end of outer cutting needle
40 inner needle
41 tissue compartment of inner needle
42 sample opening of outer cutting needle
43 wall between channels
44 pieces of carrier medium
45 side piece of carrier medium closest to the centre of the sample storage
46 piece of more rigid but still resilient supporting material
47 rotational axis of sample storage 48 single piece of carrier medium arranged to collect plurality of tissue samples
49 compression spring for displacement of sample storage
50 first drum of tissue collection device
51 second drum of tissue collection device
52 first end of roll of carrier medium
53 second end of roll of carrier medium
54 sample piston for bringing carrier medium into contact with tissue sample
55 sample roller
56 sampling extension on sample roller
57 rotational direction of inner needle
58 residual tissue sample
59 trajectory followed by centre of sample roller
60 shaft of sample roller
61 cogwheel on shaft of sample roller
62 cogwheel in engagement with cogwheel on shaft of sample roller
63 rotational direction of sample roller
64 sample container
65 lid of sample container

The invention claimed is:

1. A tissue collection device for collection of one or more tissue samples from a biopsy needle or biopsy device,
the tissue collection device including a tissue sample positioning arrangement adapted to receive and/or support a biopsy needle or biopsy device holding a tissue sample,
the tissue collection device including a carrier medium adapted to adhere to a tissue sample,
the tissue collection device being adapted to perform a tissue collection operation by relative movement between the carrier medium and the biopsy needle or biopsy device by firstly bringing the carrier medium into physical contact with a tissue sample held by a sample part of the biopsy needle or biopsy device, and by secondly bringing the carrier medium away from the sample part of the biopsy needle or biopsy device,
wherein the tissue sample positioning arrangement is adapted to support the biopsy needle or biopsy device in a fixed position relative to a housing of the tissue collection device in a transverse direction of a longitudinal axis of the biopsy needle or biopsy device, wherein the tissue collection device is adapted to perform the tissue collection operation by movement of the carrier medium in the transverse direction of the longitudinal axis of the biopsy needle or biopsy device,
wherein the tissue collection device includes a sample storage with sample compartments, each of the sample compartments having the form of a channel in which at least a portion of the carrier medium is arranged,
wherein the sample storage is configured as a drum, in which the sample compartments are arranged along the periphery of the drum,
wherein the drum is arranged to be rotated a number of angular steps corresponding to a distance between two neighbouring ones of the sample compartments,
wherein the tissue collection device is adapted to perform the tissue collection operation by displacement of the drum relative to the housing in the transverse direction of the longitudinal axis of the biopsy needle or biopsy device and back again when the drum has been rotated one or more angular steps.

2. A tissue collection device according to claim 1, wherein the carrier medium, in the form of a sheet material, covers a bottom and two opposed sides of the channel forming one of the sample compartments.

3. A tissue collection device according to claim 2, wherein the carrier medium arranged in the channel is formed as a single piece which has been folded to form a bottom part connecting two opposed side parts, whereby the bottom part of the carrier medium covers the bottom of the channel and the respective side parts of the carrier medium cover the corresponding opposed sides of the channel.

4. A tissue collection device according to claim 3, wherein the at least central part of the bottom part of the carrier medium covering the bottom of the channel has been preformed into a bulging configuration by stamping.

5. A tissue collection device according to claim 2, wherein free edges of the respective side parts of the carrier medium are held in place in the channel by respective protrusions arranged at either side of the channel.

6. A tissue collection device according to claim 2, wherein at least a central part of the bottom part of the carrier medium covering the bottom of the channel is bulged away from the bottom of the channel at least before bringing the carrier medium into physical contact with a tissue sample.

7. A tissue collection device according to claim 1, wherein the drum is adapted to be displaced relative to the housing in the direction of the biopsy needle and back again by means of a crankshaft arranged internally in the drum.

8. A tissue collection device according to claim 7, wherein the crankshaft has a first and a second opposed end journaled in the housing and a crankpin offset from an axis of rotation of the crankshaft, and wherein the crankpin is arranged in a hub of the drum.

9. A tissue collection device according to claim 8, wherein the drum is journaled rotationally about the hub, wherein the hub is fixed against rotation, and wherein the crankpin is arranged in a first groove extending diametrically in the hub.

10. A tissue collection device according to claim 9, wherein the hub is fixed against rotation by means of the first end of the crankshaft which is arranged in a second groove extending diametrically in a first end piece of the hub at right angles to the first groove and by means of a pin of the hub arranged in a third groove extending in the housing in parallel with the second groove.

11. A tissue collection device according to claim 1, wherein the drum is adapted to be rotated in angular steps by means of a spring-biased arm arranged pivotally in the housing at a first end thereof and having a second end adapted to engage a number of protrusions arranged at the periphery of the drum, and wherein each protrusion corresponds to a sample compartment.

12. A tissue collection device according to claim 11, wherein one of the sample compartments does not have a corresponding one of said protrusions, and wherein the drum has a marking at its periphery being visible from outside the housing when said one of the compartments is at a position next to the biopsy needle or biopsy device.

13. A tissue collection device according to claim 1, wherein the drum is prevented from rotation against a dedicated rotational direction by means of a ratchet mechanism.

14. A biopsy device comprising a tissue collection device according to claim 1.

15. A biopsy device according to claim 14, wherein the tissue collection device collects one or more tissue samples from a biopsy needle of the biopsy device and saves the tissue samples within the biopsy device until a desired number of tissue samples are obtained from a target tissue.

16. A biopsy device according to claim 14, wherein the biopsy device has a biopsy needle including an outer cutting needle and an inner needle with a tissue compartment for the tissue sample, wherein the outer cutting needle surrounds the inner needle and is arranged slidingly along the inner needle, wherein the outer cutting needle has a cutting end and a sample opening or sample end at a distance from the cutting end, wherein the inner needle is slidable so that the tissue compartment is displaceable form the cutting end of the outer cutting needle to the sample opening or sample end of the outer cutting needle, and wherein the tissue collection device is arranged at the sample opening or sample end of the outer cutting needle.

17. A tissue collection device according to claim 1, wherein responsive to the drum being displaced in the transverse direction toward the biopsy needle or biopsy device, the drum is not rotated, and wherein responsive to the drum being displaced in the transverse direction away from the biopsy needle or biopsy device, the drum is rotated one or more angular steps.

18. A tissue collection device according to claim 1, wherein the drum is at least partially disposed within the housing of the tissue collection device.

* * * * *